(12) United States Patent (10) Patent No.: US 10,154,778 B2
Ojima et al. (45) Date of Patent: Dec. 18, 2018

(54) ENDOSCOPIC PROCESSOR

(71) Applicant: OLYMPUS CORPORATION, Hachioji-shi, Tokyo (JP)

(72) Inventors: Mai Ojima, Tokyo (JP); Kyoko Honda, Tokyo (JP); Yugo Koizumi, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 113 days.

(21) Appl. No.: 15/297,787

(22) Filed: Oct. 19, 2016

(65) Prior Publication Data

US 2017/0035278 A1 Feb. 9, 2017

Related U.S. Application Data

(63) Continuation of application No. PCT/JP2015/067403, filed on Jun. 17, 2015.

(30) Foreign Application Priority Data

Jun. 19, 2014 (JP) .................................. 2014-126365

(51) Int. Cl.
*A61B 1/005* (2006.01)
*A61B 1/045* (2006.01)
(Continued)

(52) U.S. Cl.
CPC ............ *A61B 1/045* (2013.01); *A61B 1/0005* (2013.01); *A61B 1/00009* (2013.01);
(Continued)

(58) Field of Classification Search
CPC ... A61B 1/045; A61B 1/0005; A61B 1/00039; A61B 1/00009; A61B 1/051; A61B 1/04;
(Continued)

(56) References Cited

U.S. PATENT DOCUMENTS

2002/0033882 A1 3/2002 Wada et al.
2008/0097151 A1* 4/2008 Inoue ................. A61B 1/00039
600/109
(Continued)

FOREIGN PATENT DOCUMENTS

JP 2010258030 * 9/1998 ............. A61B 1/045
JP H10-258030 A 9/1998
(Continued)

OTHER PUBLICATIONS

Sep. 29, 2015 International Search Report issued in Patent Application No. PCT/JP2015/067403.
(Continued)

*Primary Examiner* — Peter D Le
*Assistant Examiner* — Howard D Brown, Jr.
(74) *Attorney, Agent, or Firm* — Oliff PLC

(57) ABSTRACT

An endoscopic processor includes a video signal input unit to which a video signal of an image of a subject is input, a release signal input unit to which a release signal performed by a user is input, a target area detector that detects a target area in which an amount of characteristics is greater than a predetermined threshold with respect to each frame image in the input video signal, a zoom processor that generates an enlarged image of the target area detected by the target area detector, a storage that associates and holds the enlarged image generated by the zoom processor and a frame image from which the target area has been detected, and an output unit that externally outputs, from the storage, the frame image that corresponds to a timing at which the release signal was input to the release signal input unit, and the enlarged image.

7 Claims, 15 Drawing Sheets

(51) Int. Cl.
  *A61B 1/04* (2006.01)
  *A61B 1/00* (2006.01)
  *A61B 1/05* (2006.01)
  *H04N 5/225* (2006.01)
  *H04N 5/232* (2006.01)
  *H04N 9/07* (2006.01)
  *A61B 1/06* (2006.01)

(52) U.S. Cl.
  CPC ............ *A61B 1/00039* (2013.01); *A61B 1/04* (2013.01); *A61B 1/051* (2013.01); *H04N 5/2256* (2013.01); *H04N 5/23245* (2013.01); *H04N 5/23296* (2013.01); *H04N 9/07* (2013.01); *A61B 1/063* (2013.01); *A61B 1/0638* (2013.01); *G06T 2207/10068* (2013.01); *G06T 2207/30096* (2013.01); *H04N 2005/2255* (2013.01)

(58) Field of Classification Search
  CPC .. A61B 1/063; A61B 1/0638; H04N 5/23245; H04N 5/2256; H04N 5/23296; H04N 9/07; H04N 2005/2255; G06T 2207/30096; G06T 2207/10068
  See application file for complete search history.

(56) References Cited

U.S. PATENT DOCUMENTS

| | | |
|---|---|---|
| 2009/0214111 A1 | 8/2009 | Zinaty et al. |
| 2009/0214411 A1* | 8/2009 | Zhang ...................... B82B 3/00 423/447.2 |
| 2011/0319711 A1* | 12/2011 | Yamaguchi ........ A61B 1/00009 600/109 |
| 2013/0064436 A1* | 3/2013 | Tanaka ............... A61B 1/00009 382/128 |
| 2015/0038837 A1 | 2/2015 | Inoue et al. |

FOREIGN PATENT DOCUMENTS

| | | | | |
|---|---|---|---|---|
| JP | H10258030 | * | 9/1998 | ............... A61B 1/04 |
| JP | 2002-085343 A | | 3/2002 | |
| JP | 2006-223850 A | | 8/2006 | |
| JP | 2009-201994 A | | 9/2009 | |
| JP | 2010-172673 A | | 8/2010 | |
| JP | 2010172673 | * | 8/2010 | ......... H04N 5/23245 |
| JP | 2010172673 | * | 12/2010 | ............... A61B 1/00 |
| JP | 2012-010733 A | | 1/2012 | |
| JP | 2012010733 | * | 1/2012 | ... G06T 2207/10068 |
| WO | 2012/153568 A1 | | 11/2012 | |
| WO | 2013/150745 A1 | | 10/2013 | |

OTHER PUBLICATIONS

Sep. 29, 2015 Written Opinion issued in Patent Application No. PCT/JP2015/067403.

Apr. 26, 2016 Notice of Rejection issued in Japanese Patent Application No. 2015-558278.

Jul. 19, 2016 Decision to Grant issued in Japanese Patent Application No. 2015-558278.

* cited by examiner

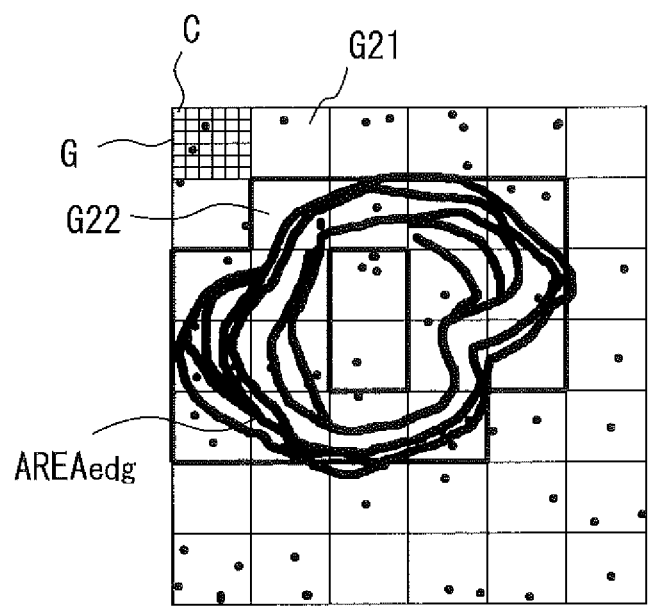
F I G. 7

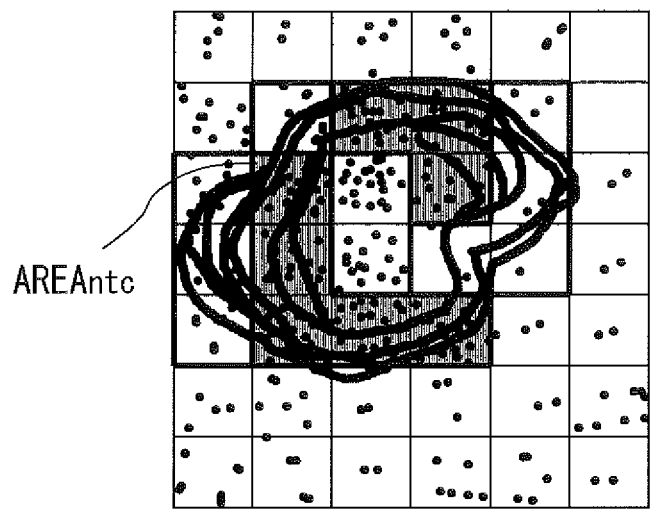
F I G. 9

ENDOSCOPIC PROCESSOR

CROSS-REFERENCE TO RELATED APPLICATIONS

This application is based upon and claims the benefit of priority of the prior Japanese Patent Application No. 2014-126365, filed on Jun. 19, 2014, the entire contents of which are incorporated herein by reference.

This is a Continuation Application of PCT Application No. PCT/JP2015/067403, filed on Jun. 17, 2015, which was not published under PCT Article 21(2) in English.

FIELD

The present invention relates to an endoscopic system that is able to perform image processing on an endoscopic image of a subject which is captured by a scope, and to display an obtained endoscopic video or still image on a monitor or to record the obtained video or image.

BACKGROUND

Conventionally, in endoscopy, an image of the inside of the body cavity of, for example, a patient that is a subject is captured by a scope, necessary image processing is performed on an obtained video signal by a processor, and the image is displayed on, for example, a monitor. If a part suspected of being a lesion has been detected in the examination, a still image of the part is, for example, recorded or printed out while displaying the image on, for example, the monitor. A user such as a doctor who performed the endoscopic examination checks the recorded still image again after the examination.

A technology has been disclosed that records coordinate information on a target area along with its observation image, the target area being a specific area, in an endoscopic image, which is designated by a cursor (see, for example, Japanese Laid-open Patent Publication No. 10-258030).

Further, another technology has also been disclosed that associates a position of an endoscope tip in the body of a subject with a still image of an endoscopic image at that position, and records them (see, for example, Japanese Laid-open Patent Publication No. 2006-223850).

In recent years, procedures in endoscopy have increasingly become complicated.

SUMMARY

An endoscopic processor according to an aspect of the present invention includes a video signal input unit to which a video signal obtained by capturing an image of a subject is input, a release signal input unit to which a release signal created by a release manipulation performed by a user is input, a target area detector that is connected to the video signal input unit and that detects a target area in which an amount of characteristics is greater than a predetermined threshold with respect to each frame image in the input video signal, a zoom processor that generates an enlarged image obtained by performing zoom processing on the target area detected by the target area detector, a storage that associates the enlarged image generated by the zoom processor with a frame image from which the target area has been detected and that holds the images, and an output unit that externally outputs, from the storage, the frame image that corresponds to a timing at which the release signal was input to the release signal input unit, and the enlarged image.

BRIEF DESCRIPTION OF DRAWINGS

FIG. 7 is a diagram that explains a method for calculating an edge-detection area;

FIG. 9 is a diagram that explains a target area detected in a white light (ordinary light) mode;

DESCRIPTION OF EMBODIMENTS

Embodiments will now be described in detail with reference to the drawings.

First Embodiment

Figure 1:
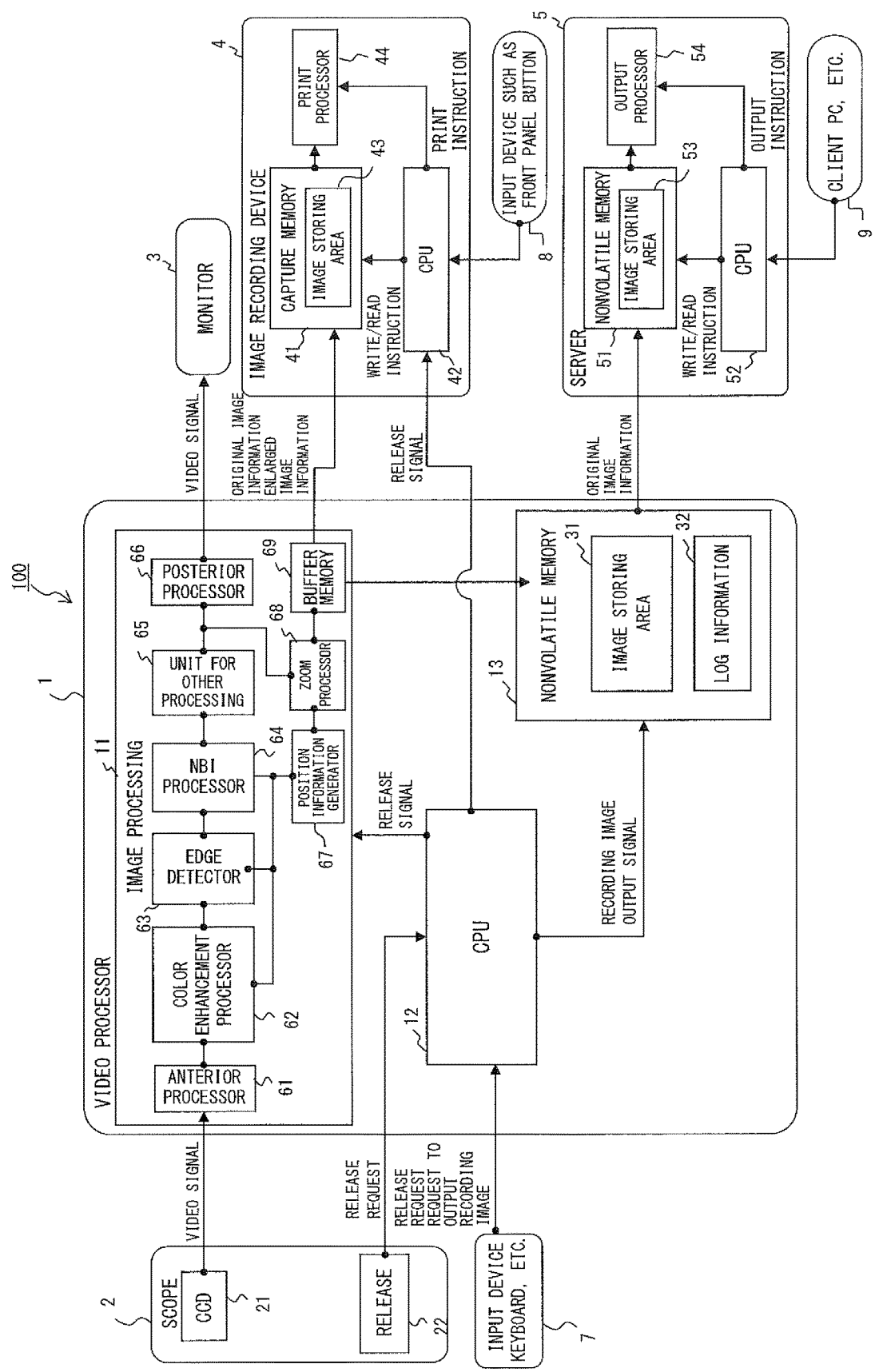
FIG. 1 is a diagram of a configuration of an endoscopic system according to a first embodiment.

FIG. 1 is a diagram of a configuration of an endoscopic system according to a first embodiment. An endoscopic system 100 illustrated in FIG. 1 includes a video processor 1, a scope 2, a monitor 3, an image recording device 4, and a server 5. The endoscopic system 100 performs image processing on a video signal using the video processor 1, and displays an obtained endoscopic image of the video signal on the monitor 3 or records it in, for example, the image recording device 4, the video signal being obtained by performing image capturing using the scope 2.

The scope 2 includes a CCD (charge coupled device) 21 and a release switch 22. The scope 2 reports to the video processor 1 about a release trigger such as a manipulation of the release switch 22 that is performed by a user. The scope 2 captures an image of a subject using the CCD 21, and transmits an obtained video signal to the video processor 1.

The video processor 1 includes a built-in CPU 12 in a control device such as an FPGA (field-programmable gate array), and also includes a video processing circuit 11 and a nonvolatile memory 13. The video processor 1 includes, for example, an input device 7 such as a keyboard, an output device for performing an output to the monitor 3, a communication device for communicating with the image recording device 4, an output device for outputting a video signal to the image recording device 4, and a communication device for communicating with the server 5 that is an external storage. The video processor 1 records a video as a still image according to the above-described reported release trigger, so as to store it in a set storage space.

The video processing circuit 11 performs necessary image processing on a video signal input from the scope 2. The video processing circuit 11 includes an anterior processor 61, a color enhancement processor 62, an edge detector 63, an NBI (narrow band imaging) processor 64, a unit 65 for other processing, a posterior processor 66, a position information generator 67, a zoom processor 68, and a buffer memory 69.

The details are described with reference to, for example, FIG. 2, but in the present embodiment, a user of the endoscopic system 100, such as a doctor, identifies a part believed to be a lesion from an endoscopic image obtained by processing a video signal received from the scope 2, and obtains its enlarged image, using the position information generator 67 and the zoom processor 68 that are included in the configuration of the video processing circuit 11. Each component that constitutes the video processing circuit 11 is also described in detail with reference to, for example, FIG. 2.

The nonvolatile memory 13 includes an image storing area 31 that temporarily stores, for example, a still image, from an endoscopic image, that is to be recorded in the server 5, and a log information storing area 32, the endoscopic image being obtained by performing image processing in the video processing circuit 11. Log information that is stored in the log information storing area 32 will be described in a second embodiment.

The CPU 12 receives, for example, a release request from, for example, the scope 2 that is connected to the video processor 1, and transmits a release signal to the video processing circuit 11 and the image recording device 4 on the basis of the received release request. Further, the CPU 12 controls each component that constitutes the video processor 1.

The monitor 3 receives a video signal of an endoscopic image, and displays, for example, an endoscopic video on the basis of the received video signal, wherein necessary processing is performed on the video signal in the video processor 1.

The image recording device 4 includes a CPU 42, a capture memory 41 that is a nonvolatile memory, and a print processor 44. As an external interface, it has a communication device for communicating with the video processor 1 and an input device for inputting a video signal from the video processor 1, and an input device 8 such as a button provided in a front panel of the image recording device 4. When a request has been received from the user through the input device 8, the print processor 44 performs processing necessary to print out image data stored in an image storing area 43 of the capture memory 41.

The server 5 includes a CPU 52, a nonvolatile memory 51, and an output processor 54. As an external interface, it has a communication device for communicating with, for example, a client PC 9 that is connected to the server 5. When a request has been received from the user through, for example, the client PC 9, the output processor 54 performs processing for outputting image data to, for example, a desired device, the image data being stored in, for example, an image storing area 53 of the nonvolatile memory 51.

Figure 2:
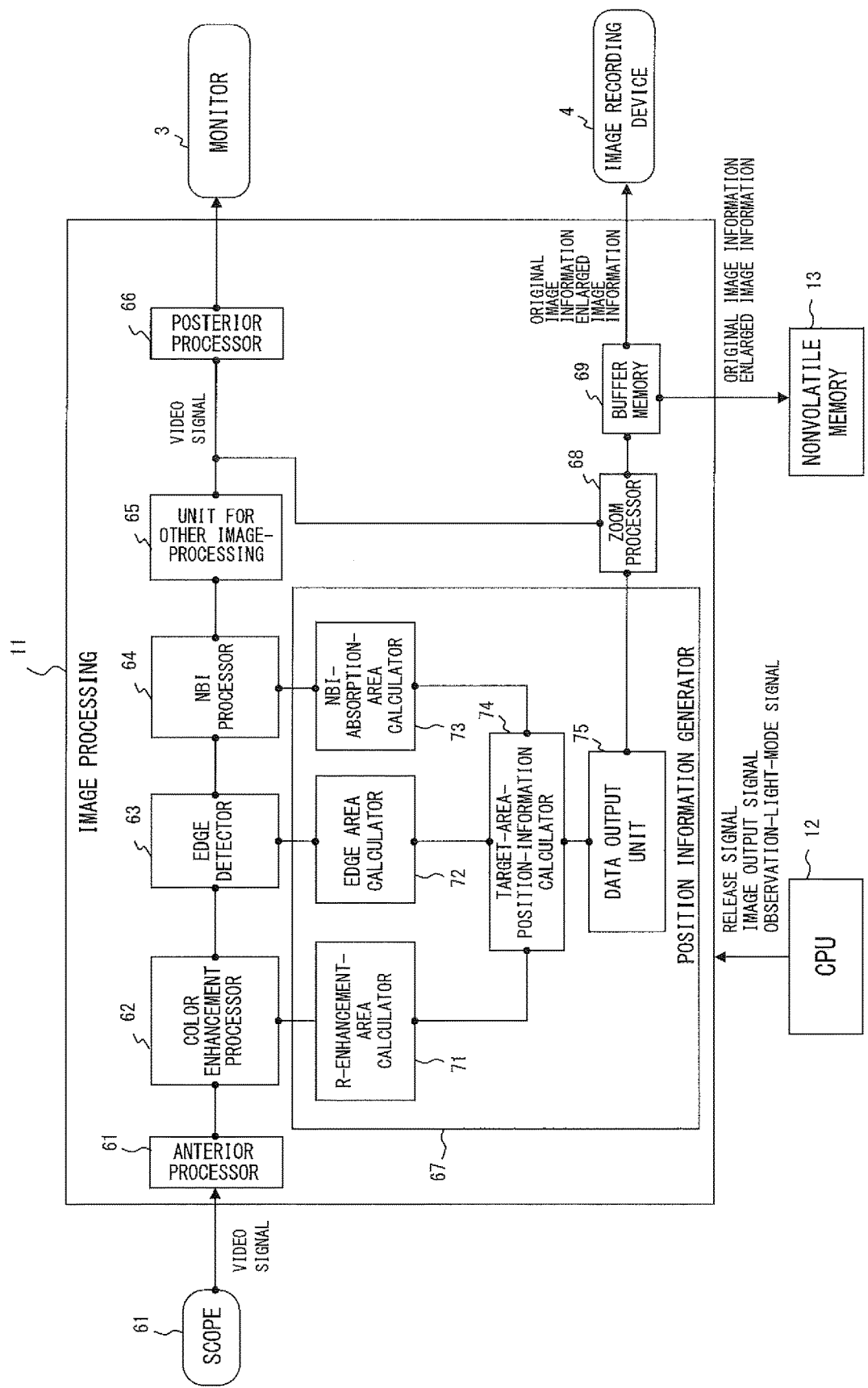
FIG. 2 is a detailed block diagram of a video processing circuit.

FIG. 2 is a detailed block diagram of the video processing circuit 11.

The anterior processor 61 of the video processing circuit 11 performs anterior processing that is to be performed before necessary image processing is performed on a video signal input from the scope 2. The color enhancement processor 62 performs processing of enhancing a color in an image. The edge detector 63 performs processing of enhancing an edge structure formed with a contour of, for example, a projection or convexoconcave that appears in an image. The NBI processor 64 processes an image obtained by radiating a narrow-band light when an observation light mode is an NBI (narrow band imaging). The unit 65 for other image-processing performs necessary image processing other than the color enhancement processing, the edge detection, and the processing for an NBI image. The detailed description of processing performed by the unit 65 for other image-processing is omitted because a known technology is used.

In the endoscopic system 100 according to the present embodiment, a video signal output from the unit 65 for other image-processing is input to the posterior processor 66 regardless of the presence or absence of a release signal. The video processor 1 transmits, to the monitor 3, a video signal obtained by performing necessary posterior processing in the posterior processor 66. At the same time, the video signal output from the unit 65 for other image-processing is also transmitted to the buffer memory 69 through the zoom processor 68 regardless of whether a release signal based on a release request made by, for example, the release switch 22 of the scope 2 has been received from the CPU 12.

The position information generator 67 generates information that indicates a position of a target area using data generated in the process of image processing, so as to output the generated information to the zoom processor 68. When an image includes a target area, the zoom processor 68 generates a zoom image of the target area so as to output the zoom image to the buffer memory 69. The zoom processor 68 synchronizes data of the zoom image of the generated zoom image of the target area with data of an entire image input from the unit 65 for other image-processing, and transmits them to the buffer memory 69. Accordingly, in the present embodiment, when a target area is detected in addition to an endoscopic image (an entire image), the video processor 1 is also able to externally output a zoom image of the target area according to a release signal based on a release request made by, for example, the release switch 22.

The position information generator 67 that generates information indicating a position of a target area includes an R-enhancement-area calculator 71, an edge area calculator 72, an NBI-absorption-area calculator 73, a target-area-position-information calculator 74, and a data output unit 75. The position information generator 67 uses, according to the type of image, a result of processing performed in each of the color enhancement processor 62, the edge detector 63, and the NBI processor 64 described above, so as to define information indicating whether there exists a target area in an frame image, or information indicating the position of the target area if there exists the target area, and to output such information.

Specifically, the R-enhancement-area calculator 71 of the position information generator 67 obtains an area in which a value of red (R) is high in an image, the value being obtained by the color enhancement processing performed in the color enhancement processor 62. The edge area calculator 72 obtains an area in which an edge appears in the image, the edge being obtained by the edge-detection processing performed in the edge detector 63. The NBI-absorption-area calculator 73 uses an image on which the NBI-image processing has been processed in the NBI processor 64, so as to obtain an area in which green (G) or blue (B) is absorbed at a high rate in an NBI image.

The target-area-position-information calculator 74 obtains necessary information from the R-enhancement-area calculator 71, the edge area calculator 72, and the NBI-absorption-area calculator 73 according to the type of image to be processed, and uses the information to calculate position information on a target area in a frame image. The data output unit 75 outputs, to the zoom processor 68, the position information on the target area that is obtained in the target-area-position-information calculator 74.

As described above, the zoom processor 68 generates a zoom image of the target area from a video signal on which image processing has been performed and the position information on the target area, wherein the video signal is output from the unit 65 for other image-processing and the position information is output from the data output unit 75 of the position information generator 67. Data of the generated zoom image of an enlarged area is temporarily held in the buffer memory 69 along with data of a corresponding entire image, and the pieces of data are output together to the image recording device 4 or the nonvolatile memory 13 according to a release signal or an image output signal.

As described above, in the endoscopic system 100 according to the present embodiment, the video processor 1 searches for a target area with respect to each frame image, the frame images being consecutive. From among the frame images that have target areas, an image of a frame that corresponds to a release signal or an image output signal is output to, for example, the image recording device 4 or the nonvolatile memory 13 in the video processor 1 along with a zoom image of the target area.

Referring to the figures, a method is specifically described below, mainly with respect to an operation of the position information generator 67 in the video processing circuit 11, the method including searching for a target area in an image, generating a zoom image of the target area, and recording it in, for example, the image recording device 4.

Figure 3:
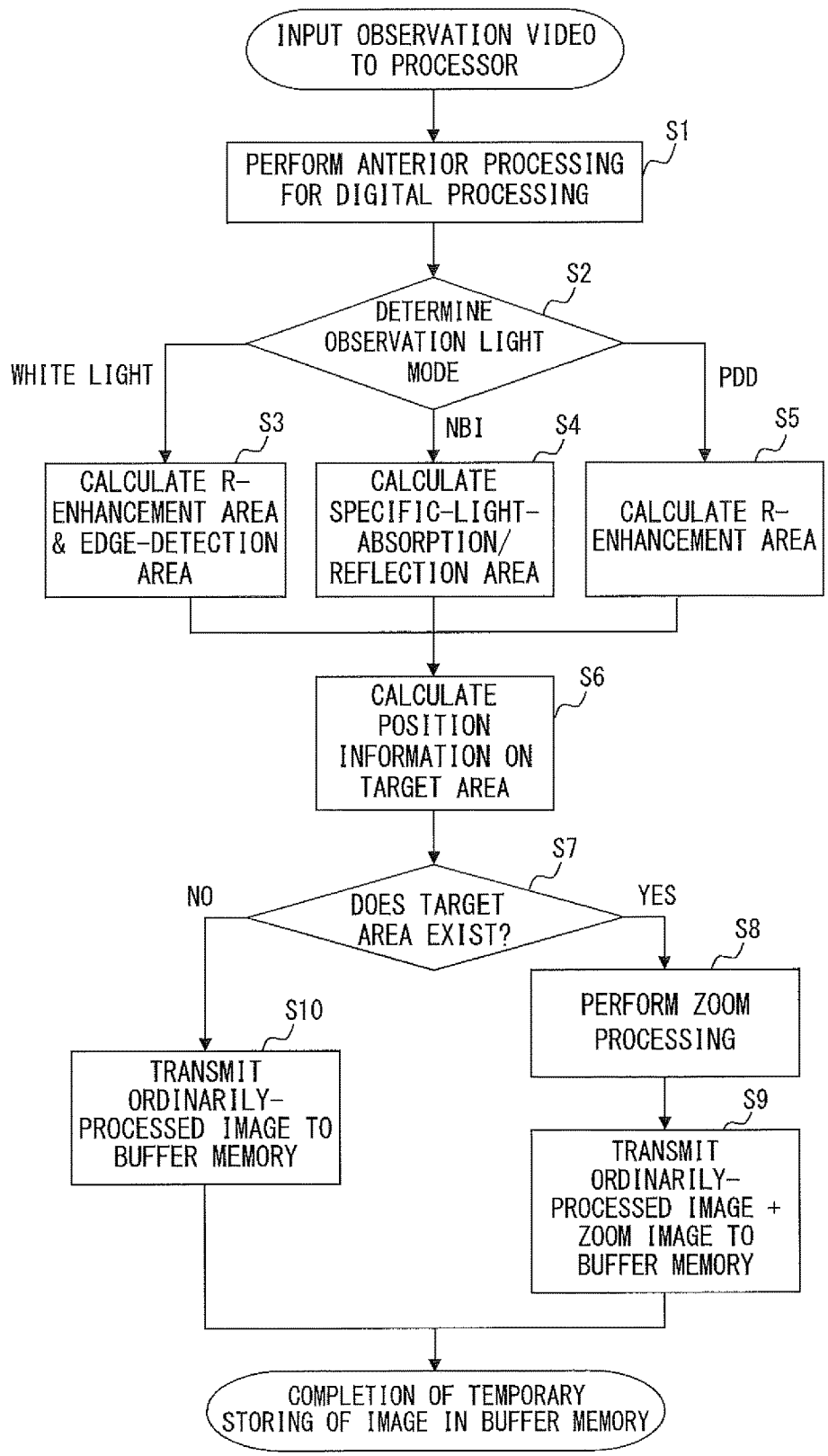
FIG. 3 is a flowchart that illustrates an operation of processing a video signal which is performed by a video processor in the endoscopic system according to the first embodiment.

FIG. 3 is a flowchart that illustrates an operation of processing a video signal which is performed by the video processor 1 in the endoscopic system 100 according to the present embodiment. The video processing circuit 11 of the video processor 1 performs a series of processing illustrated in FIG. 3 every time one-frame observation image is input from the scope 2.

First, in Step S1, the video processing circuit 11 performs processing anterior to digital processing of a video signal that is performed in the anterior processor 61. Then, in Step S2, the video processing circuit 11 determines the observation light mode. The determination in Step S2 is performed on the basis of an observation-light-mode signal reported by the CPU 12. In the example, as illustrated in FIG. 3, the video processing circuit 11 determines which of the following three observation light modes is set: a white light (ordinary light) mode, an NBI mode, or a PPD (photodynamic diagnosis) mode. The process moves on to Step S3, S4, or S5 when the observation light mode is the white light mode, the NBI mode, or the PPD mode, respectively.

The following are descriptions on how to detect a target area from an image and how to output an image of the detected target area for each observation light mode.

(Processing of White-Light (Ordinary-Light) Observation Image)

In general, an endoscopic image captured in a white light mode is characterized in that a lesion has more intense redness than other parts and is not level. Using the characteristics, an area with intense redness and an area with, for example, convexoconcave are determined, so as to detect a target area from the endoscopic image.

In Step S3 of FIG. 3, the video processing circuit 11 causes the R-enhancement-area calculator 71 and the edge area calculator 72 to perform calculation. As described above, the R-enhancement-area calculator 71 and the edge area calculator 72 perform calculation using pieces of image data that are obtained by performing processing in the color enhancement processor 62 and by performing processing in the edge detector 63, respectively. Referring to FIGS. 4 to 7, processing of calculating an R-enhancement area that is performed by the R-enhancement-area calculator 71 and processing of calculating an edge-detection area that is performed by the edge area calculator 72 will be described in detail later.

When the R-enhancement area and the edge-detection area are calculated in Step S3, the process moves on to Step S6. In Step S6, the video processing circuit 11 causes the target-area-position-information calculator 74 to calculate position information on a target area. The position information on a target area is calculated on the basis of the R-enhancement area and the edge-detection area that are obtained in Step S3. A method for calculating position information on a target area will be described in detail later with reference to FIGS. 8 and 9.

In Step S7, the video processing circuit 11 refers to the position information on a target area that is calculated in Step S6, so as to determine whether a target area is included in an image. The process moves on to Step S8 when the image includes the target area, and moves on to Step S10 when the image does not include the target area.

In Step S8, the video processing circuit 11 causes the zoom processor 68 to generate a zoom image of the target area. The zoom image of the target area is generated on the basis of data of an entire image output from the unit 65 for other image-processing of the video processing circuit 11 and on the basis of the position information on the target area that is output from the data output unit 75. Then, in Step S9, the video processing circuit 11 transmits, to the buffer memory 69, the data of the entire image and the zoom image of the target area that is generated in Step S8, and terminates the processing.

When the image does not include the target image, the video processing circuit 11 only transmits the data of the entire image to the buffer memory 69 in Step S10, and terminates the processing.

In the example, a zoom image of a target area is generated in Step S8, but the zoom image does not always have to be generated.

As described above, the video processing circuit 11 searches for a target area for an image of each frame. When it detects a target area from an image, the video processing circuit 11 outputs not only data of an entire image but also data of a (zoom) image of the target area by synchronizing the (zoom) image with the entire image, so that the (zoom) image is associated with the entire image and the images are held in the buffer memory 69. When the data of the (zoom) image of the target area that is associated with the data of the entire image is included in the buffer memory 69, it is output along with the data of the entire image upon outputting the data of the entire image to the outside of the video processing circuit 11.

Methods for calculating an R-enhancement area and an edge-detection area that are used when a target area is detected from an endoscopic image in a white light (ordinary light) mode are described with reference to FIGS. 4 to 7.

Figure 4:
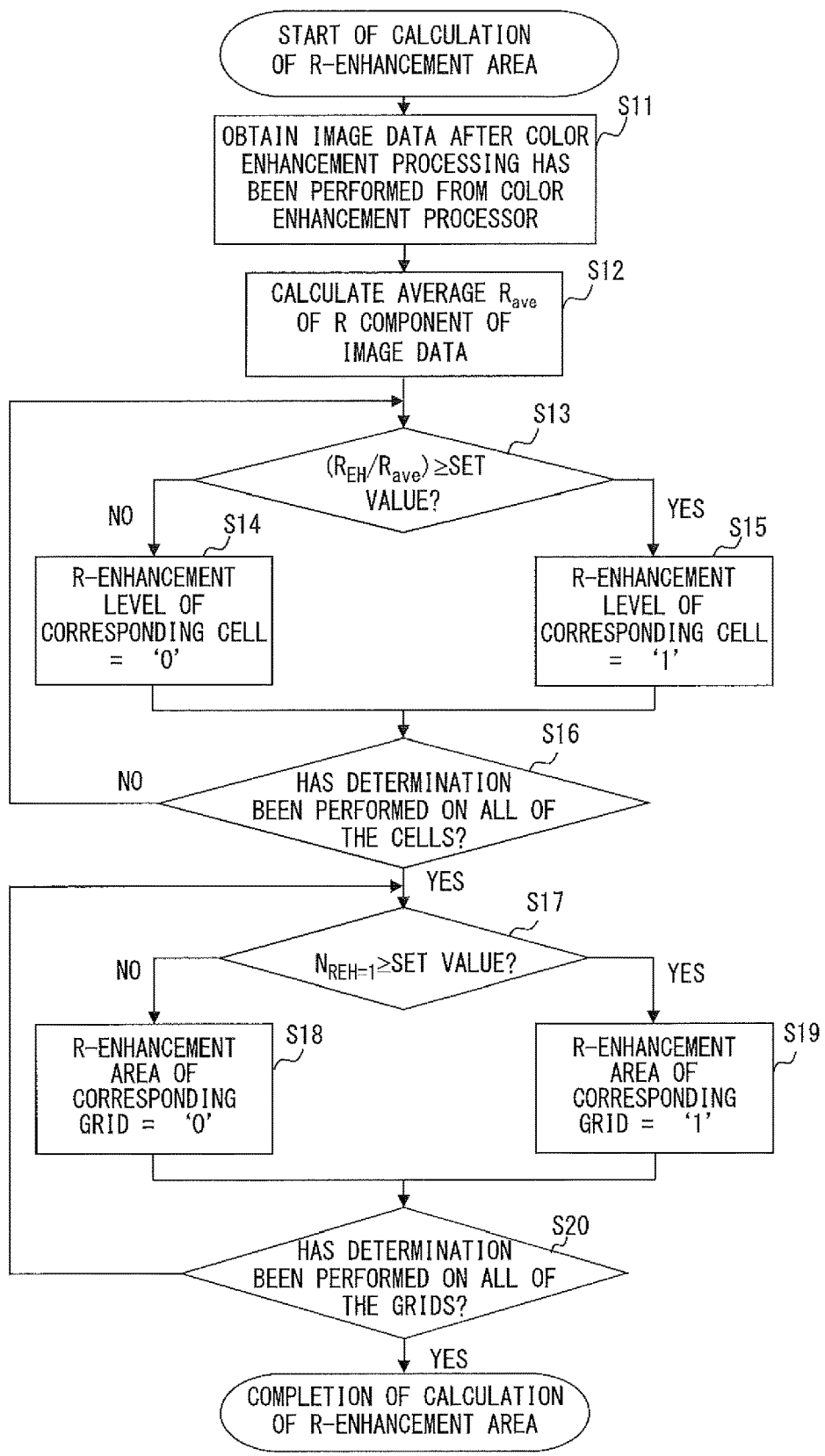
FIG. 4 is a flowchart that illustrates processing of calculating an R-enhancement area that is performed by an R-enhancement-area calculator.

FIG. 4 is a flowchart that illustrates the processing of calculating an R-enhancement area that is performed by the R-enhancement-area calculator 71. The R-enhancement-area calculator 71 starts performing a series of processing illustrated in FIG. 4 when the process moves on to Step S3 from Step 2 in FIG. 3.

First, in Step S11, the R-enhancement-area calculator 71 obtains image data after color enhancement processing has been performed from the color enhancement processor 62. Then, in Step S12, the R-enhancement-area calculator 71 calculates an average $R_{ave}$ of a red (R) component of the entirety of an image, and the process moves on to Step S13.

In the processing of calculating an R-enhancement area, first, it is determined, in the processes of Step S13 to Step S16, whether the level of redness for each cell is not less than a predetermined level. In the following example, one section constituted of a plurality of pixels is referred to as a "cell", and an area of a predetermined size which includes a predetermined number of cells is referred to as a "grid".

In Step S13, the R-enhancement-area calculator 71 determines, for each cell, whether a ratio $R_{EH}/R_{ave}$ of an average $R_{EH}$ of a value of a red (R) component and the average $R_{ave}$ calculated in Step S12 is not less than a predetermined set value. The process moves on to Step S15 when the ratio $R_{EH}/R_{ave}$ is not less than the predetermined set value, and moves on to Step S14 when the ratio $R_{EH}/R_{ave}$ is less than the predetermined set value. This is described with reference to FIG. 5.

Figure 5:
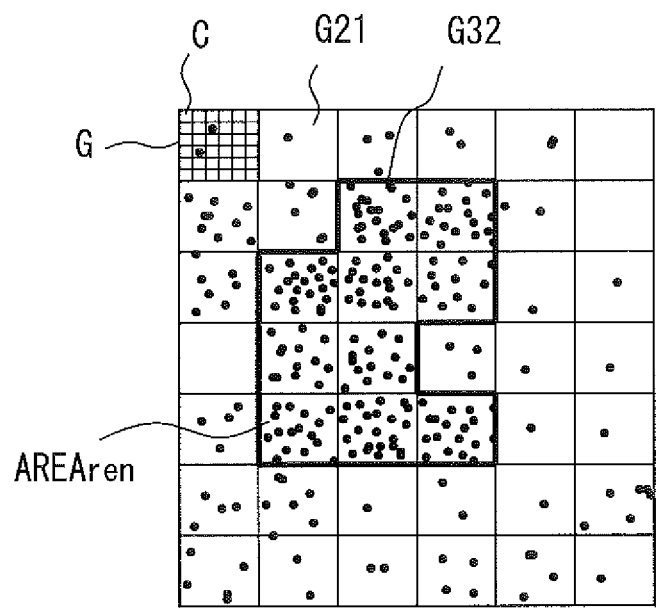
FIG. 5 is a diagram that explains a method for calculating an R-enhancement area.

FIG. 5 is a diagram that explains the method for calculating an R-enhancement area.

As described above, in the example, the value $R_{EH}$ of an R component is compared with the average $R_{ave}$ of an R component of the entirety of an image for each cell C. When the ratio "$R_{EH}/R_{ave}$" of the value $R_{EH}$ of an R component of a cell C to the average $R_{ave}$ of an R component of the entirety of the image is not less than a predetermined set value, the cell C is determined to be a cell with intense redness. When the ratio "$R_{EH}/R_{ave}$" is less than the predetermined set value, the cell C is determined to be a cell with mild redness. Any value may be set to be the predetermined set value, and the same applies to a set value that will be used in processing performed after this. In FIG. 5, a cell with intense redness is represented by a black spot, and the other portion (a white portion that does not include a black spot) in a grid G represents a cell with mild redness.

Then, in Step S14 (when $R_{EH}/R_{ave}$<set value), the R-enhancement-area calculator 71 sets the value "0" for an R-enhancement level of a cell C that is used for the comparison in Step S13, and in Step S15 (when $R_{EH}/R_{ave}$≥set value), the R-enhancement-area calculator 71 sets the value "1". The R-enhancement level of a cell represents whether the cell C is a cell with intense redness.

In Step S16, the R-enhancement-area calculator 71 determines whether the determination in Step S13 has been performed on all of the cells in the image, that is, whether the setting of an R-enhancement level has been performed for all of the cells C. When there exists an undetermined cell C, the process returns to Step S13 and the processes described above are performed for the undetermined cell C. When the setting of an R-enhancement level for all of the cells C has been completed, the process moves on to Step S17.

In the processes of Step S17 to Step S20, it is determined whether the level of redness is not less than a predetermined level for each grid.

In Step S17, the R-enhancement-area calculator 71 determines, for each grid, whether a density $N_{REH=1}$ of a cell C in which the R-enhancement level value is "1" is not less than a predetermined set value, using the R-enhancement level set in the previous steps. Here, compare, for example, grids G21 and G32 in FIG. 5. In the grid G21, the number of cells C in each of which the R-enhancement level value is "1" is only one, so the density $N_{REH=1}$ is relatively low in the grid G21. On the other hand, in the grid G32, there exist many cells C in each of which the R-enhancement level value is "1", so the density $N_{REH=1}$ is relatively high in the grid G32. In the example, it is assumed that the density $N_{REH=1}$ in the grid G21 is less than a predetermined set value and the grid G21 is an area with mild redness, and the density $N_{REH=}$1 in the grid G32 is not less than the predetermined set value and the grid G32 is an area with intense redness.

Then, with respect to a grid G used for the determination in Step S17, in Step S18 (when $N_{REH=1}$<set value), the R-enhancement-area calculator 71 sets the value "0" for R-enhancement area information, and in Step S19 (when $N_{REH=1}$≥set value), the R-enhancement-area calculator 71 sets the value "1" The R-enhancement-area information on a grid G represents whether the grid G is a grid with intense redness in the processing of calculating a target area. In the example above, the value "0" is set for the R-enhancement-area information on the grid G21, and the value "1" is set with respect to the grid G32.

In Step S20, the R-enhancement-area calculator 71 determines whether the determination in Step S17 has been performed on all of the grids in the image, that is, whether the setting of R-enhancement-area information has been performed for all of the grids G. When there exists an undetermined grid G, the process returns to Step S17 and the processes described above are performed for the undetermined grid G. When the setting of R-enhancement-area information for all of the grids G has been completed, the processing is terminated. In FIG. 5, a set of grids G in each of which the value "1" is set for the R-enhancement-area information, that is, an area "$AREA_{ren}$" detected as an R-enhancement area is emphasized by enclosing with a thick line.

In FIG. 4, first, a determination of the intensity of redness is performed for each cell, and a determination of a grid that includes many cells each of which has intense redness (density $N_{REH=1}$≥set value) is then performed for each grid, but the method for detecting an R-enhancement area is not limited to this. For example, instead of determining the intensity of redness for each cell, it is also acceptable to compare an average $R_{gave}$ of a red (R) component for each grid with the average $R_{ave}$ for the entirety of an image so as to determine the grid to be an R-enhancement area when a ratio $R_{gave}/R_{ave}$ is not less than a predetermined value. It is possible to detect an R-enhancement area with a high degree of accuracy when the determination of an R-enhancement area is performed by the method of FIG. 4, and it is possible to shorten a calculation time when the determination of a ratio $R_{gave}/R_{ave}$ is performed for each grid.

Figure 6:
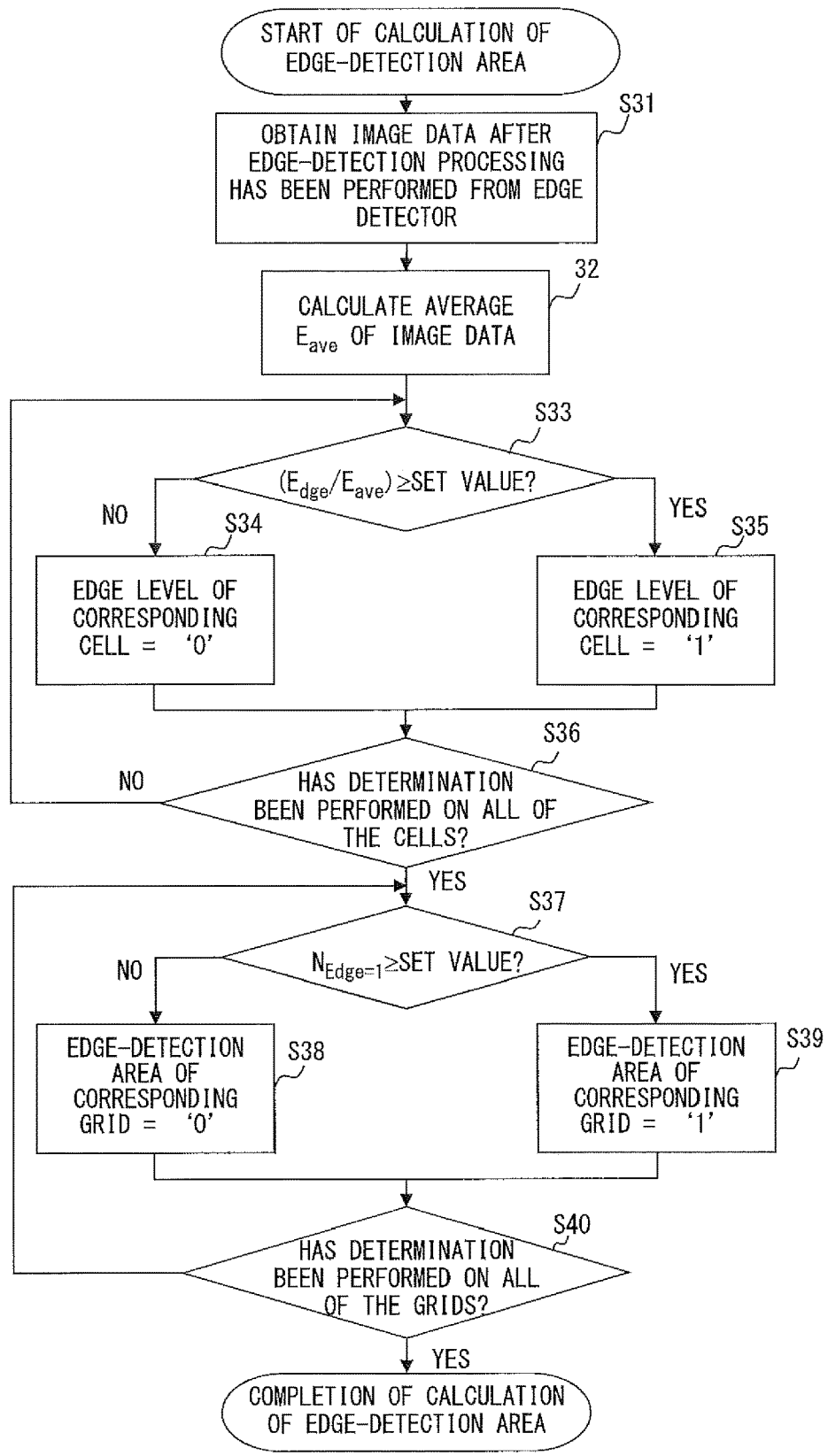
FIG. 6 is a flowchart that illustrates processing of calculating an edge-detection area that is performed by an edge area calculator.

FIG. 6 is a flowchart that illustrates the processing of calculating an edge-detection area that is performed by the edge area calculator 72. The edge area calculator 72 starts performing a series of processing illustrated in FIG. 6 when the process moves on to Step S3 from Step 2 in FIG. 3.

First, in Step S31, the edge area calculator 72 obtains image data after edge-detection processing has been performed from the edge detector 63. Then, in Step S32, the edge area calculator 72 calculates an average $E_{ave}$ of an edge level of the image data.

In the example, in processing performed after this, the intensity of edge is determined for each cell C in the processes of Step S33 to Step S35, as is the case in the above-described processing of calculating an R-enhancement area (FIG. 4). Then, in the processes of Step S36 to Step S40, it is determined, for each grid G, whether a grid G is an edge-detection area, using a result of determining the intensity of edge for each cell C.

In Step S33, the edge area calculator 72 determines whether a ratio "$E_{dge}/E_{ave}$" of an intensity of edge $E_{dge}$ for each cell and the average $E_{ave}$ of the intensity of edge of the entirety of the image is not less than a predetermined set value, the average $E_{ave}$ being calculated in Step S32. The process moves on to Step S35 when the ratio "$E_{dge}/E_{ave}$" is not less than the predetermined set value, and moves on to Step S34 when it is less than the predetermined set value.

FIG. 7 is a diagram that explains the method for calculating an edge-detection area.

As described above, the intensity of edge $E_{dge}$ of a cell C is compared with the intensity of edge $E_{ave}$ of the entirety of an image. When the ratio $E_{dge}/E_{ave}$ of the intensity of edge of a cell C to the intensity of edge $E_{ave}$ of the entirety of an image is not less than a predetermined set value, the cell C is determined to be a cell from which an edge has been detected. When the ratio $E_{dge}/E_{ave}$ is less than the predetermined set value, it is determined that an edge has not been detected from the cell C. In FIG. 7, a cell from which an edge has been detected is represented by a black spot, and the other portion (a white portion that does not include a black spot) in a grid G represents a cell from which an edge has not been detected.

Then, in Step S34 (when $E_{dge}/E_{ave}$<set value), the edge area calculator 72 sets the value "0" for an edge level of a cell C that is used for the comparison in Step S33, and in Step S35 (when $E_{dge}/E_{ave}$≥set value), the edge area calculator 72 sets the value "1". The edge level of a cell represents whether an edge has been detected from the cell C.

In Step S36, the edge area calculator 72 determines whether the determination in Step S33 has been performed on all of the cells in the image, that is, whether the setting of an edge level has been performed for all of the cells C. When there exists an undetermined cell C, the process returns to Step S33 and the processes described above are performed for the undetermined cell C. When the setting of an edge level for all of the cells C has been completed, the process moves on to Step S37.

In Step S37, the edge area calculator 72 determines, for each grid, whether a density $N_{Edge=1}$ of a cell C in which the edge level value is "1" is not less than a predetermined set value, using the edge level set in the previous steps. For example, it is determined that the number of cells in each of which the edge level value is "1", that is, the density $N_{Edge=1}$ of a cell with a high edge level, is less than the predetermined set value in the grid G21 of FIG. 7. On the other hand, it is determined that the density $N_{Edge=1}$ of a cell with a high edge level is not less than the predetermined set value in the grid G22.

Then, with respect to a grid G used for the determination in Step S37, in Step S38 (when $N_{Edge=1}$≤set value), the edge area calculator 72 sets the value "0" for edge-detection-area information, and in Step S39 (when $N_{Edge=1}$≥set value), the edge area calculator 72 sets the value "1". The edge-detection-area information on a grid G represents whether the grid G has an edge structure in the processing of calculating a target area. Even if a grid G is detected as an edge area by the edge area calculator 72, an edge structure is not always detected from the grid G by the edge detector 63.

In Step S40, the edge area calculator 72 determines whether the determination in Step S37 has been performed on all of the grids in the image, that is, whether the setting of edge-detection-area information has been performed for all of the grids G. When there exists an undetermined grid G, the process returns to Step S37 and the processes described above are performed for the undetermined grid G. When the setting of edge-detection-area information for all of the grids G has been completed, the processing is terminated. In FIG. 7, a set of grids G in each of which the value "1" is set for the edge-detection-area information, that is, an area "$AREA_{ege}$" detected as an edge-detection area is emphasized by enclosing with a thick line.

As described above, in the example, also in the processing of calculating an edge-detection area, first, determination is performed for each cell, and next, determination is performed for each grid, as is the case in the processing of calculating an R-enhancement area, but the method is not limited to this. For example, instead of determining the intensity of edge for each cell, it is also acceptable to compare an average $E_{gave}$ of an intensity of edge in each grid with the intensity of edge $E_{ave}$ for the entirety of an image so as to determine the grid to be an edge-detection area when a ratio $E_{gave}/E_{ave}$ is not less than a predetermined value. It is possible to detect an edge-detection area with a high degree of accuracy when the determination of an edge-detection area is performed by the method of FIG. 6, and it is possible to shorten a calculation time when the determination of a ratio $E_{gave}/E_{ave}$ is performed for each grid.

Further, the processing of calculating an R-enhancement area of FIG. 4 and the processing of calculating an edge-detection area of FIG. 6 may be performed in series, or the two calculating processings may be performed in parallel.

Using the R-enhancement-area information and the edge-detection-area information that are respectively set by the processing of FIG. 4 and the processing FIG. 6, a method for detecting a target area in a white light (ordinary light) mode is described with reference to FIGS. 8 to 9.

Figure 8:
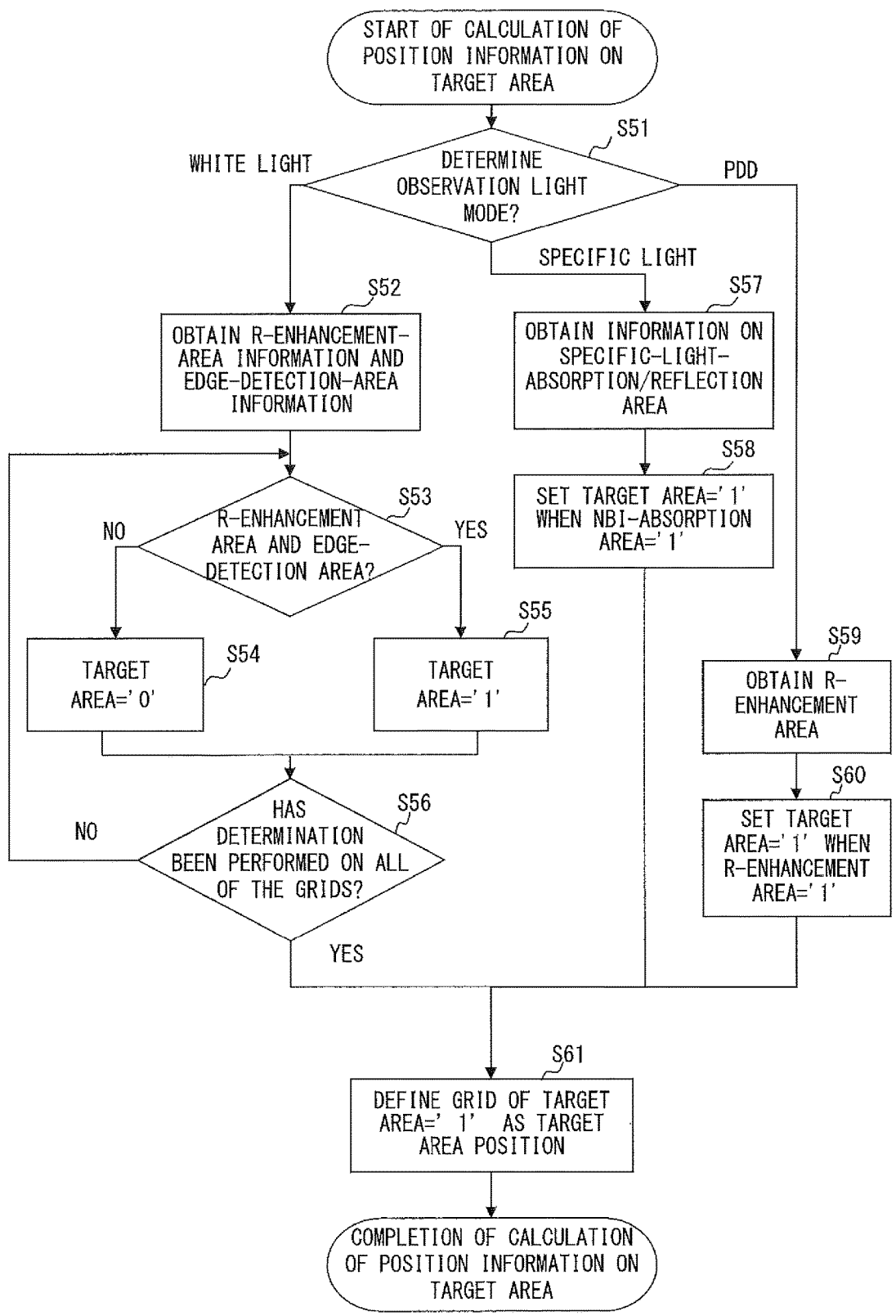
FIG. 8 is a flowchart that illustrates processing of calculating position information on a target area that is performed by a target-area-position-information calculator.

FIG. 8 is a flowchart that illustrates processing of calculating position information on a target area that is performed by the target-area-position-information calculator 74. The target-area-position-information calculator 74 starts performing a series of processing illustrated in FIG. 8 when the process moves on to Step S6 from Step 3 (or Step 4 or Step S5) in FIG. 3.

First, in Step S51, the target-area-position-information calculator 74 determines the observation light mode. In Step S51, the determination is performed similarly to the determination performed in Step S2 of FIG. 3. Depending on which of the observation light modes is set: a white light (ordinary light) mode, an NBI mode, or a PPD mode, the process moves on to Step S52, Step S57, or Step S59, respectively. The case of a white light (ordinary light) mode, that is, the processing performed in and after Step S52, is described here, and each of the cases of an NBI mode and a PPD mode will be described when a method for calculating position information on a target area in the corresponding observation light mode is described.

In Step S52, the target-area-position-information calculator 74 obtains R-enhancement-area information and edge-detection-area information from the R-enhancement-area calculator 71 and the edge area calculator 72, the R-enhancement-area information and the edge-detection-area information being results of calculations performed in the R-enhancement-area calculator 71 and the edge area calculator 72, respectively.

In Step S53, the target-area-position-information calculator 74 determines, for each grid, whether a grid G corresponds to an R-enhancement area $AREA_{ren}$ and an edge-enhancement area $AREA_{edg}$ at the same time. Specifically, it determines whether the value "1" is set for both the R-enhancement-area information and the edge-enhancement-area information. The process moves on to Step S55 when the value "1" is set for both of the pieces of area information, and the process moves on to Step S54 in the other cases.

In Step S54, the target-area-position-information calculator 74 sets the value "0" for target area information on a grid G that is used for the determination in Step S53, and in Step S55, the target-area-position-information calculator 74 sets the value "1". The target area information on a grid G represents whether the grid G is a target area.

When the value of target area information is set in Step S54 or Step S55, the process moves on to Step S56. Then, the target-area-position-information calculator 74 determines whether the determination in Step S53 has been performed on all of the grids in the image, that is, whether the setting of target area information has been performed for all of the grids G. When there exists an undetermined grid G, the process returns to Step S53 and the processes described above are performed for the undetermined grid G. The process moves on to Step S61 when the setting of target area information for all of the grids G has been completed.

In Step S61, the target-area-position-information calculator 74 defines, as a target area position, a grid G for which "1" is set to be the value of its target area information, and terminates the processing.

FIG. 9 is a diagram that explains a target area detected in a white light (ordinary light) mode. As illustrated in FIG. 9, an area (a grid G) that is included in the R-enhancement area $AREA_{ren}$ of FIG. 5 and the edge-detection area $AREA_{edg}$ of FIG. 7 at the same time is determined to be a target area $AREA_{ntc}$. In FIG. 9, eight grids G that have been determined to be target areas $AREA_{ntc}$ are indicated by coloring.

When the target area position has been defined by performing the processes of Step S51 to Step S56 and Step S61, the determination of whether there exists a target area is performed in Step S7 of FIG. 3 as described above with respect to FIG. 3, and necessary image data is transmitted to the buffer memory 69 according to a determination result. A method for transmitting, to a predetermined recording destination, image data temporarily stored in the buffer memory 69 is described with reference to FIG. 10.

Figure 10:
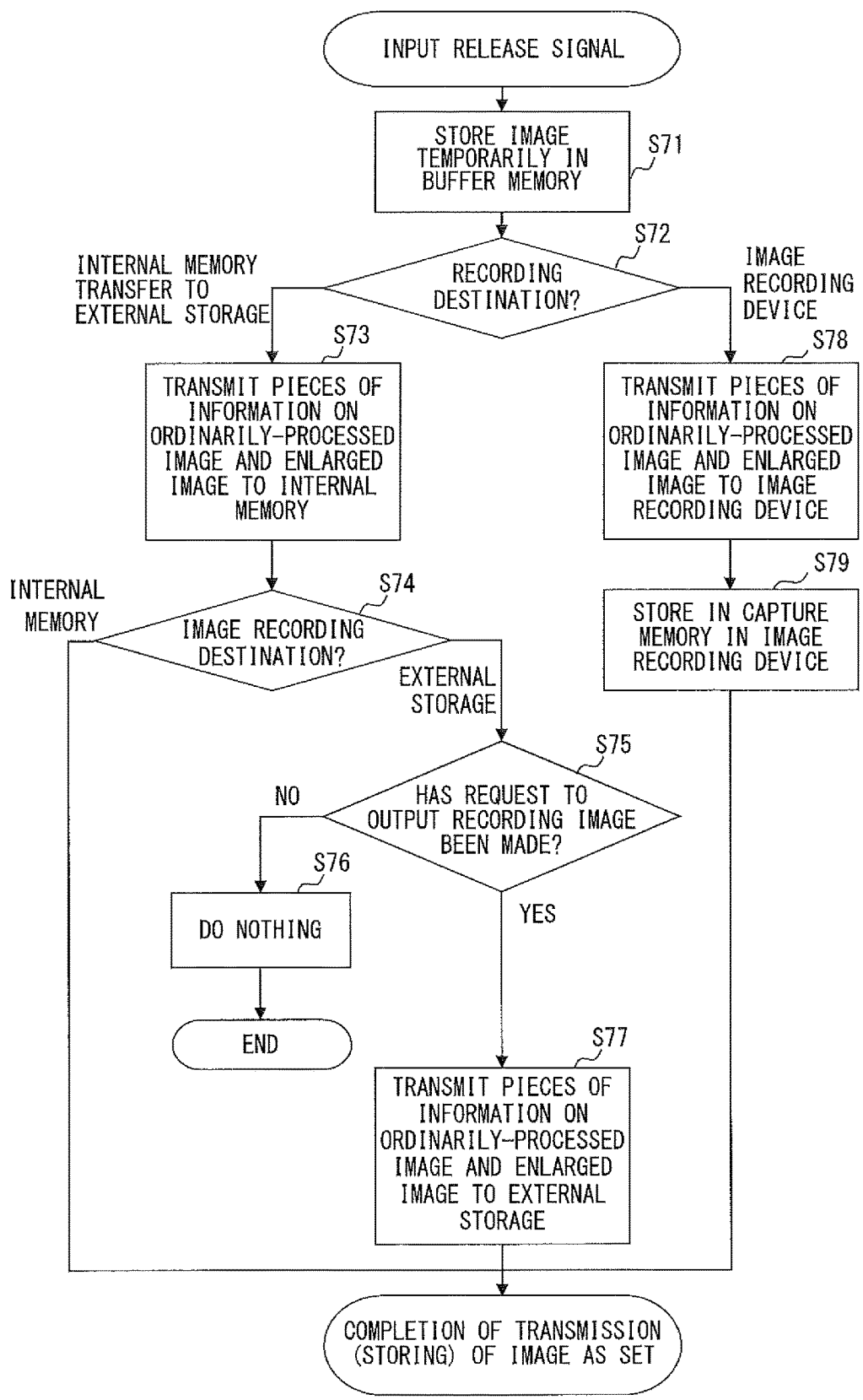
FIG. 10 is a flowchart that illustrates processing of transmitting image data stored in a buffer memory to a recording destination.

FIG. 10 is a flowchart that illustrates processing of transmitting image data stored in the buffer memory 69 to a recording destination. As described above, the video processing circuit 11 performs the processing of FIG. 3 on each input frame image. When it receives a release request from, for example, the release switch 22 of the scope 2, the CPU 12 of the video processor 1 transmits a release signal to the video processing circuit 11 on the basis of the request. Then, the release switch 22 starts performing a series of processing of FIG. 10 on a frame image that corresponds to a timing at which the release request was received.

First, in Step S71, the CPU 12 temporarily stores, in the buffer memory 69, pieces of data of an entire image and a zoom image of a target area that have been transmitted to the buffer memory 69 by the video processing circuit 11 in Step S9 of FIG. 3. Then, in Step S72, the CPU 12 determines the recording destination of the pieces of data temporarily stored in the buffer memory 69. The recording destination of data is preset in the video processor 1, and in the example, it is assumed that an internal memory of the video processor 1 or the image recording device 4 of FIG. 1 is set. Here, when the internal memory of the video processor 1 is the recording destination, not only the case of ultimately recording data in the internal memory, but also the case of ultimately recording data in the server 5 through the internal memory is included. The process moves on to Step S73 when the recording destination of the pieces of data temporarily stored in the buffer memory 69 is "internal memory", and the process moves on to Step S78 when the recording destination is "image recording device".

In Step S73, the CPU 12 causes the pieces of data of the entire image and the zoom image of a target area in the buffer memory 69 to be transmitted to the nonvolatile memory 13 that is an internal memory, and stores them in the image storing area 31 of the nonvolatile memory 13. Then, in Step S74, the CPU 12 further determines the recording destination of the pieces of image data transmitted from the buffer memory 69. In the example, it is assumed that, as the recording destination of the pieces of image data, the nonvolatile memory 13 itself that is an internal memory or the server 5 that is an external storage is preset in the video processor 1. When the recording destination of the pieces of image data is "internal memory", the CPU 12 terminates the processing without performing any particular process. When the recording destination of the pieces of image data is "external storage", the CPU 12 moves on to Step S75.

In Step S75, the CPU 12 determines whether a request to output a recording image has been made. When a request to output a recording image has been input from, for example, the input device 7 of FIG. 1, the CPU 12 transmits an image output signal to the nonvolatile memory 13 on the basis of the request. In Step S75, the CPU 12 performs determination on the basis of whether a request to output a recording image has been input from, for example, the input device 7. The process moves on to Step S77 when a request to output a recording image has been made, and the process moves on to Step S76 when it has not been made.

In Step S77, the CPU 12 transmits, to the server 5 that is an external storage, the pieces of data of the entire image and the zoom image of a target area that have been stored in the image storing area 31 of the nonvolatile memory 13, and terminates the processing. In the server 5, the CPU 52 stores the received pieces of data in the image storing area 53 of the nonvolatile memory 51, and when it receives a request to output an image from, for example, the client PC 9, the CPU 52 reads the pieces of image data from the image storing area 53 and outputs them to the output processor 54. When it transmits data of an image having a target area to, for example, the client PC 9, the output processor 54 performs a variety of processing related to an output of data, such as processing of associating a zoom image of the target area with a corresponding entire image.

On the other hand, the CPU 12 terminates the processing of FIG. 10 without performing any particular process in Step S76. This means that, with respect to a frame image at a timing at which a request to output a recording image was not received from the input device 7, the image (and a zoom image of a target area) is not to be recorded in the server 5. In this case, after that, the pieces of data stored in the image storing area 31 of the nonvolatile memory 13 will be, for example, overwritten so as to be deleted.

The process moves on to Step S78 when the recording destination is the image recording device 4 in Step S72, and the CPU 12 transmits, to the image recording device 4, the pieces of data of the entire image and the zoom image of a target area in the buffer memory 69. Then, in Step S79, the CPU 42 of the image recording device 4 stores, in the image storing area 43 of the capture memory 41, the pieces of data transmitted from the video processor 1 in Step S78, and terminates the processing. After that, when a request to print out an image has been received through the input device 8 such as a front panel button of the image recording device 4, the CPU 42 of the image recording device 4 issues a print instruction to the print processor 44. The print processor 44 associates the entire image with the zoom image of a target area and performs, for example, a variety of processing necessary to print out images in a lined-up state, so as to cause the images stored in the image storing area 43 of the capture memory 41 to be printed out.

The method for transmitting data from the buffer memory 69 to each recording destination when a target area has been extracted by the above-described method is described in FIG. 10, and the same method is used when a target area has not been detected.

It is possible not only to output pieces of data of an entire image and a zoom image of a target area that is associated with the entire image to the image recording device 4 or the server 5 that is external to the video processor 1, or to output them to the nonvolatile memory 13 that is an internal memory, so as to record them, but also to display them on the monitor 3. This is described with reference to FIG. 11.

Figure 11:
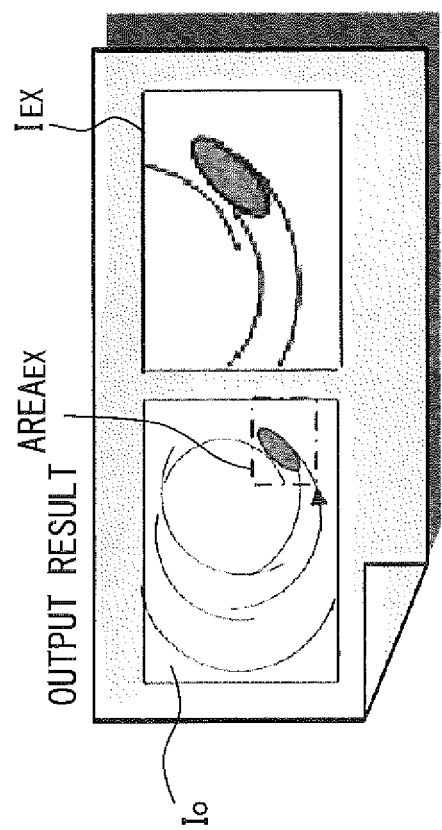
FIG. 11 illustrates a method for outputting a detected target area.
Figure 11:
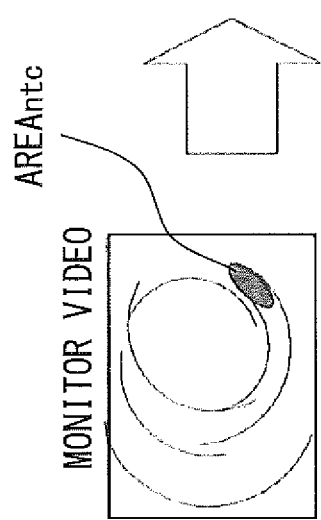

FIG. 11 illustrates a method for outputting a detected target area.

FIG. 11 illustrates a monitor video that is output to the monitor 3, and an entire image I$_O$ and a zoom image I$_{EX}$ of a target area AREA$_{ntc}$ that is detected in the position information generator 67 of the video processor 1, wherein the monitor video is obtained by performing necessary image processing on a video signal using the video processor 1, the video signal being obtained by performing image capturing using the scope 2.

As described above, a predetermined range that includes the detected target area AREA$_{ntc}$ is a range AREA$_{EX}$ for which a zoom image is to be generated, and the range AREA$_{EX}$ is enlarged so as to generate a zoom image I$_{EX}$.

As described above, the endoscopic system 100 according to the present embodiment may read data from the nonvolatile memory 13 so as to display, on the monitor 3, an output result described on the right side of FIG. 11, according to an instruction from a user. Further, it may read data from, for example, the image recording device 4 so as to print out an output result described on the right side of FIG. 11, according to an instruction from the user.

Further, any method may be used for outputting (to display and record) an entire image and a (zoom) image of a target area that is associated with the entire image. For example, the method may include generating, in the video processor 1, an image obtained by overlapping two images in PinP (picture in picture) or PoutP (picture out picture), so as to display the image on the monitor 3 or to record it in the image recording device 4 or the server 5.

Further, in order for a user such as a doctor to easily check a detected target area, a method other than the above-described method for generating a (zoom) image of the target area in addition to an entire image may be used. For example, the method may include generating, when a target area is detected, an image in which marking is performed around the target area in an entire image, so as to output the generated marking image to, for example, the monitor 3 or the image recording device 4. Such a method also permits a user such as a doctor to easily check a target area after an examination, as is the above-described case of associating an entire image with an image of a target area to output them together.

(Processing of NBI Image)

Next, the case in which the observation light mode is an NBI mode is described.

In an endoscopic image captured in an NBI mode, green (G) or blue (B) is absorbed well into, for example, a blood vessel formed around, for example, a tumor, which results in highlighting a lesion. Using the characteristics, a target area is detected from a captured endoscopic image.

The processes of Step S1 and Step S2 of FIG. 3, that is, the processes from performing the anterior processing on a video signal received from the scope 2 to determining the observation light mode, are as described in the explanation about the white light (ordinary light) mode.

The processes of Step S4 and Step S6 of FIG. 3 are now described in detail, that is, focusing on how to calculate target-area-position information when the observation light mode is an NBI mode.

Figure 12:
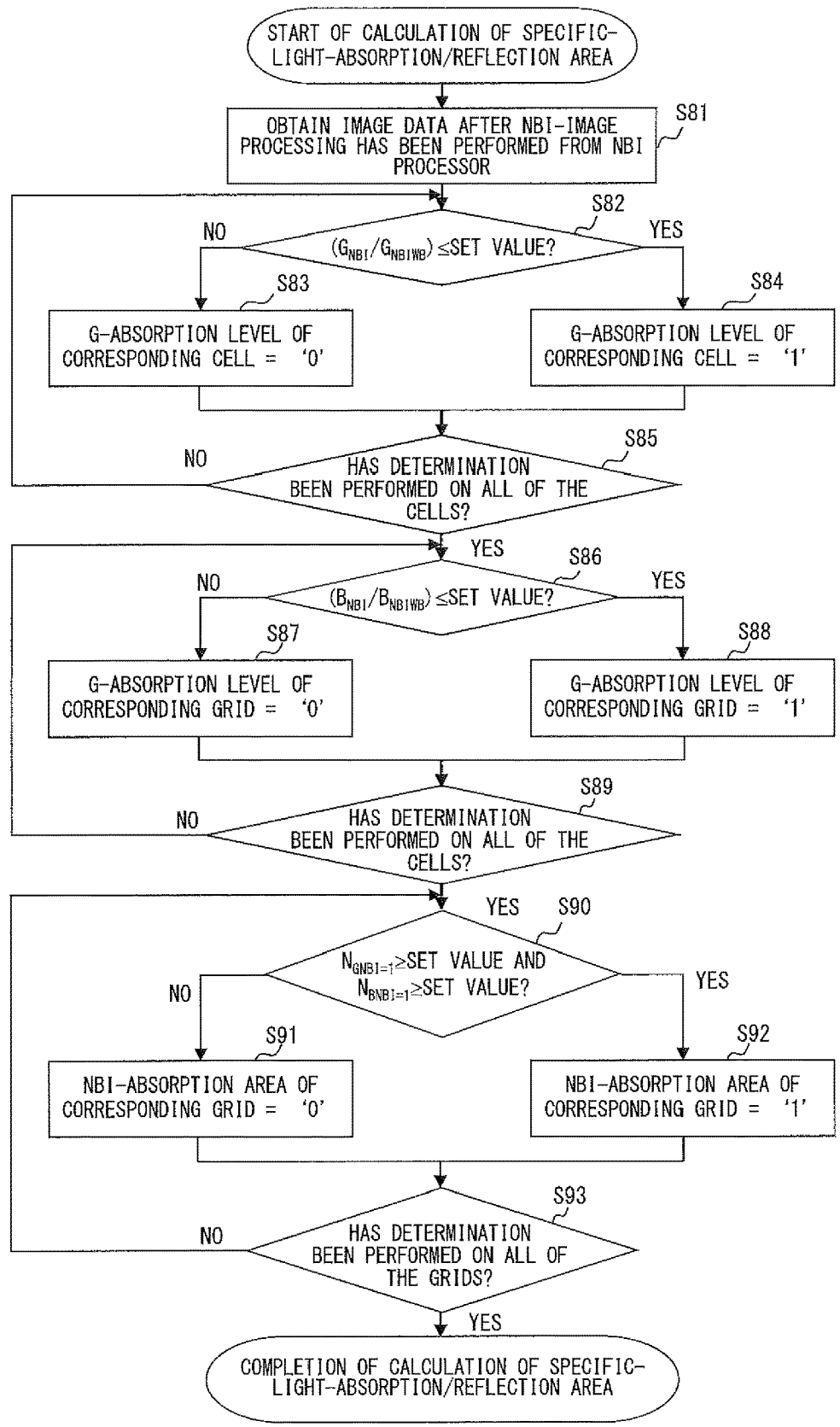
FIG. 12 is a flowchart that illustrates processing of calculating a specific-light-absorption/reflection area that is performed by an NBI-absorption-area calculator.

FIG. 12 is a flowchart that illustrates processing of calculating a specific-light-absorption/reflection area that is performed by the NBI-absorption-area calculator 73. The NBI-absorption-area calculator 73 starts performing a series of processing illustrated in FIG. 12 when the process moves on to Step S4 from Step 2 in FIG. 3.

First, in Step S81, the NBI-absorption-area calculator 73 obtains, from the NBI processor 64, image data after NBI-image processing has been performed. At this point, white balance values G$_{NBIWB}$ and B$_{NBIWB}$ for green (G) and blue (B) that are used in the subsequent steps, Step S82 and Step S86, may be obtained along with the image data. Alternatively, the white balance values may be calculated in the NBI-absorption-area calculator 73 from image data upon measuring the obtained white balance.

First, a determination of whether the absorption level of green (G) for each cell is greater than a predetermined level is performed by performing the processes of Step S82 to Step S85.

In Step S82, the NBI-absorption-area calculator 73 determines, for each cell, whether a ratio G$_{NBI}$/G$_{NBIWB}$ of a value G$_{NBI}$ of a reflection level of a green (G) component in the image data and a value G$_{NBIWB}$ of a white balance for green (G) is not greater than a predetermine set value. In the example, the determination is performed on the basis that, in white balance processing, red (R), green (G), and blue (B) lights are radiated onto a white subject and color adjustment is performed according to a color balance in a reflected light. Further, white balance data of an NBI observation light may be used. In other words, if the determination is performed on the basis that, when the reflection level of green (G) of a cell in an image is not greater than the predetermined set value with respect to the level of a reflection of a green (G) light on a white subject, it is possible to determine that the absorption level of the cell is high (the reflection level is low). The process moves on to Step S84 when the ratio "G$_{NBI}$/G$_{NBIWB}$" is not greater than the predetermined set value, and moves on to Step S83 when the ratio "$G_{NBI}/G_{NBIWB}$" is greater than the predetermined set value.

In Step S83 (when $G_{NBI}/G_{NBIWB}$>set value) and Step S84 (when $G_{NBI}/G_{NBIWB}$≤set value), the NBI-absorption-area calculator 73 sets the value "0" and the value "1", respectively, for G-absorption levels of a cell that are used for the comparison in Step S82.

Then, in Step S85, the NBI-absorption-area calculator 73 determines whether the determination in Step S82 has been performed on all of the cells in the image, that is, whether the setting of a G-absorption level has been performed for all of the cells. When there exists an undetermined cell, the process returns to Step S82 and the processes described above are performed for the undetermined cell. When the setting of the G-absorption level for all of the cells has been completed, the process moves on to Step S86.

In the processes of Step S86 to Step S89, the NBI-absorption-area calculator 73 performs processing for an absorption level of blue (B), the processing being similar to the processing performed for the absorption level of green (G) in Step S82 to Step S85. Specifically, for each cell, "1" is set to be a value of the B-absorption level when a ratio "$B_{NBI}/B_{NBIWB}$" of a value $B_{NBI}$ of a reflection level of blue (B) and a value $B_{NBIWB}$ of a white balance for blue (B) is not greater than a predetermined set value, and the value "0" is set when the ratio is greater than the predetermined set value.

The setting of the absorption level of green (G) for each cell in Step S82 to Step S85 and the setting of an absorption level of blue (B) for each cell in Step S86 to Step S89 may be performed in parallel.

When the setting of an absorption level for all of the cells has been completed with respect to green (G) and blue (B), the process moves on to Step S90.

In Step S90, the NBI-absorption-area calculator 73 determines, for each grid, whether a density $N_{GNBI=1}$ of a cell in which the value of a G-absorption level is "1" is not less than a predetermined set value and a density $N_{BNBI=1}$ of a cell in which the value of a B-absorption level is "1" is not less than a predetermined set value. The process moves on to Step S92 when a density of a cell in which both of the values of absorption levels of green (G) and blue (G) are "1" is not less than the predetermined values that are set for the respective colors, and the process moves on to Step S91 in the other cases.

In Step S91 or Step S92, the NBI-absorption-area calculator 73 sets the value "0" or "1", respectively, for NBI-absorption-area information on a grid on which the determination has been performed in Step S90. The NBI-absorption-area information on a grid represents whether the grid is an area in which the absorption levels of green (G) and blue (B) in the grid are high.

In Step S93, the NBI-absorption-area calculator 73 determines whether the determination in Step S90 has been performed on all of the grids in the image, that is, whether the setting of NBI-absorption-area information has been performed for all of the grids. When there exists an undetermined grid, the process returns to Step S90 and the processes described above are performed for the undetermined grid, and when the setting of NBI-absorption-area information for all of the grids has been completed, the processing is terminated.

In the example, also in the above-described processing of calculating a specific-light absorption/reflection area (in the example, an NBI-absorption area), first, determination is performed for each cell, and next, determination is performed for each grid, as is the case in the processing of calculating an R-enhancement area or the processing of calculating an edge-detection area in a white light mode. However, the method for calculating a specific-light absorption/reflection area is not limited to this. For example, it is also acceptable to obtain an absorption level $G_{gNBI}$ of green (G) and an absorption level $B_{gNBI}$ of blue (B) in a grid for each grid, and to compare them with a value $G_{NBIWB}$ of a white balance of G and a value $B_{NBIWB}$ of a white balance of B, respectively. If both ratios $G_{gNBI}/G_{NBIWB}$ and $B_gNBI/B_{NBIWB}$ are not greater than predetermined values that are set for the respective colors, it is possible to detect an NBI-absorption area with a high degree of accuracy when the determination of an NBI-absorption area is performed by the method of FIG. 12, and it is possible to shorten a calculation time when the determination of the ratios $G_{gNBI}/G_{NBIWB}$ and $B_{gNBI}/B_{NBIWB}$ are performed for each grid.

When the setting of NBI-absorption-area information has been performed for each grid in the image, the process moves on to Step S6 from Step S4 of FIG. 3. In Step S6, the target-area-position-information calculator 74 performs the processing of calculating position information on a target area, using the NBI-absorption-area information. The process moves on to Step S57 from Step S51 in the flow of FIG. 8 in the processing of calculating position information on a target area when the observation light mode is an NBI mode.

In Step S57 of FIG. 8, the target-area-position-information calculator 74 obtains the NBI-absorption-area information from the NBI-absorption-area calculator 73. Then, in Step S58, the target-area-position-information calculator 74 sets the value "1" for target area information with respect to a grid for which the value "1" is set for its NBI-absorption-area information, and the process moves on to Step S61. In Step S61, as is the case in a white light (ordinary light) mode described above, the target-area-position-information calculator 74 defines, as a target area position, a grid for which "1" is set to be the value of its target area information, and terminates the processing.

Processing performed after the target area position has been defined in Step S61 of FIG. 8 is similar to the processing in a white light (ordinary light) mode.

(Processing of Image in Photodynamic Diagnosis (PDD))

Next, the case in which the observation light mode is a PDD mode is described.

In the photodynamic diagnosis (PDD), a drug that accumulates in cancer cells is administered and a blue light that causes a reaction with it is radiated, so as to cause a cancer tissue to glow red. Thus, redness in a lesion is highlighted in an endoscopic image captured in a PDD mode. Using the characteristics, a target area is detected from a captured endoscopic image.

The processes of Step S1 and Step S2 of FIG. 3, that is, the processes from performing the anterior processing on a video signal received from the scope 2 to determining the observation light mode, are as described in the explanation about the white light (ordinary light) mode.

The processes of Step S5 and Step S6 of FIG. 3 are now described in detail, that is, focusing on how to calculate target-area-position information when the observation light mode is a PDD mode.

As described above, redness in a lesion is highlighted in an endoscopic image captured in a PDD mode. Thus, in Step S5 of FIG. 3, the R-enhancement-area calculator 71 performs the processing of calculating an R-enhancement area of FIG. 4, so as to perform a setting of R-enhancement-area information. Then, in Step S6 of FIG. 3, the target-area-position-information calculator 74 performs the processing of calculating position information on a target area, using the R-enhancement-area information. The process moves on to Step S59 from Step S51 in the flow of FIG. 8 in the processing of calculating position information on a target area when the observation light mode is a PDD mode.

In Step S59, the target-area-position-information calculator 74 obtains the R-enhancement-area information from the R-enhancement-area calculator 71. Then, in Step S60, the target-area-position-information calculator 74 sets the value "1" for target area information with respect to a grid for which the value "1" is set for its R-enhancement-area information, and the process moves on to Step S61. In Step S61, as is the case in an NBI mode described above, the target-area-position-information calculator 74 defines, as a target area position, a grid for which "1" is set for its target area information. When the target area position has been defined, the processing of FIG. 8 is terminated.

Processing performed after the processing of FIG. 8 has been terminated is similar to the processing in a white light (ordinary light) mode or an NBI mode.

As described above, in the endoscopic system 100 according to the present embodiment, a target area is detected from an endoscopic image in the video processor 1, using data obtained upon performing image processing on a video signal obtained by performing image capturing using the scope 2, wherein a user such as a doctor has an interest in the target area that is an area having, for example, a lesion, due to the characteristics of an image in each observation light mode. Specifically, the target area is detected on the basis of the presence or absence of color or edge, or on the basis of the level of an absorption/reflection of light. The video processor 1 for an endoscopic image generates a (zoom) image of the detected target area, and associates the (zoom) image with an entire image (an endoscopic image) to hold them. When the user performs a release manipulation using, for example, the release switch 22 of the scope 2, the video processor 1 outputs an entire image (an endoscopic image) of a frame at that timing and the image of the detected target area to, for example, the image recording device 4 external to the video processor 1. Accordingly, the user such as a doctor does not have to get engaged in works during an endoscopic examination such as identifying a target area or works after the examination such as searching for an image having an area suspected of being a lesion, which results in being able to easily check, after the examination, an image in which an area suspected of being a lesion appears. This contributes to the improvement of the efficiency in an operation after an examination and to the prevention of under diagnosis.

Second Embodiment

According to the first embodiment described above, a target area is detected from an endoscopic image in the video processor 1, which results in providing the advantage of improving the efficiency in an operation after an examination and of preventing of under diagnosis. On the other hand, an endoscopic system according to the present embodiment, a report about an examination is generated in the endoscopic system 100 on the basis of log information such as a content of examination and an examination date and time, which results in improving the efficiency in an operation after the examination.

A method executed by the endoscopic system according to the present embodiment is specifically described below, the method including generating log information and generating an endoscopy report on the basis of the log information.

The configuration of the endoscopic system is as described in FIG. 1 or 2 and is similar to that of the above-described embodiment, so the description is omitted.

Figure 13A:
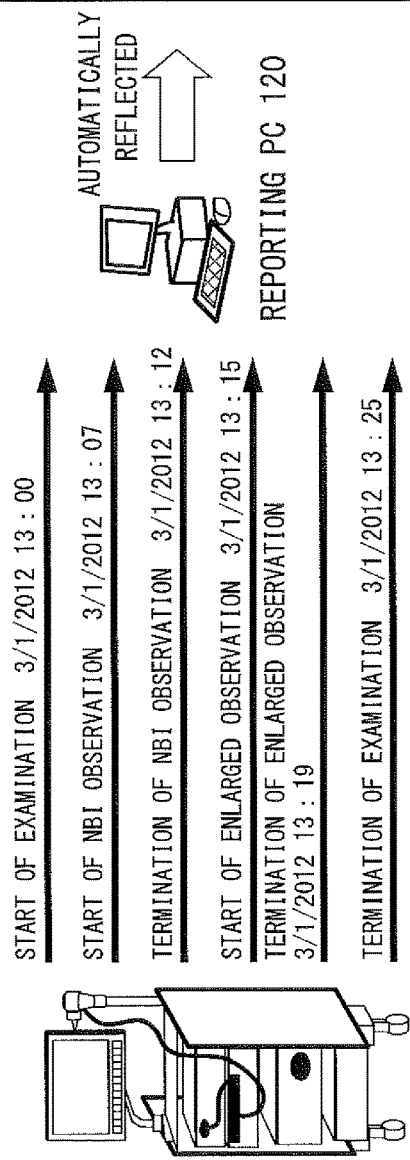
FIG. 13A is a diagram (part 1) that explains a method for generating an endoscopy report, the method being executed by the endoscopic system according to a second embodiment.
Figure 13B:
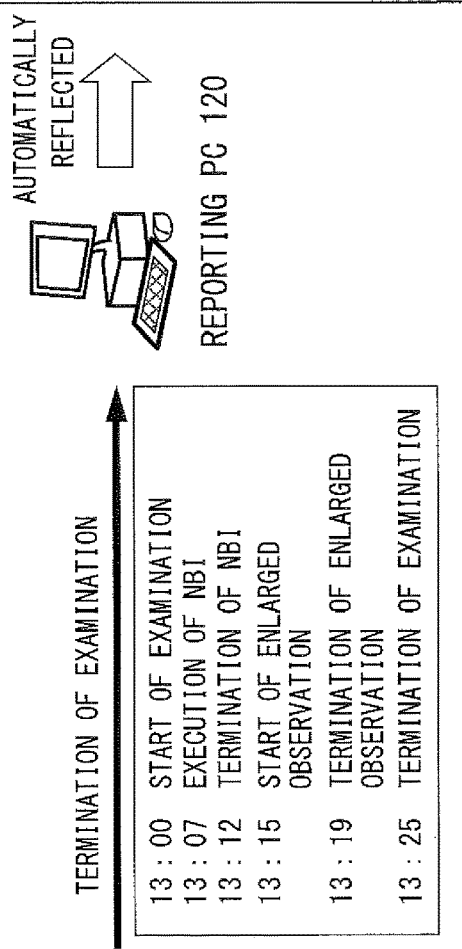
FIG. 13B is a diagram (part 2) that explains the method for generating an endoscopy report, the method being executed by the endoscopic system according to the second embodiment.

FIGS. 13A and 13B are diagrams that explain a method for generating an endoscopic report, the method being executed by the endoscopic system 100 according to the present embodiment. The client PC 9 of FIG. 1A corresponds to a reporting PC 120 illustrated in FIGS. 13A and 13B.

According to an aspect illustrated in FIG. 13A, when an endoscopic examination starts in the endoscopic system 100, the CPU 12 in the video processor 1 generates log information and transmits the information to the server 5 every time an event from among various events related to the examination occurs. Then, the information is transmitted sequentially to the reporting PC 120 (in FIG. 1, the client PC 9 corresponds to it).

Specifically, first, when an examination starts, the video processor 1 transmits, to the server 5, information such as a start of examination, time information that indicates a date and time, and information that identifies a patient or a doctor. The reporting PC 120 obtains, from the server 5, a report indicating a start of examination and the pieces of information transmitted along with the report. When it receives the report indicating a start of examination, the reporting PC 120 starts generating an endoscopy report, so as to input, to the endoscopy report, the information that identifies a patient or a doctor, an examination date, an examination start time, and other pieces of information. A predetermined format of an endoscopy report is prepared in advance, and the reporting PC 120 performs a setting of information corresponding to a predetermined position in the format, to which the information is to be input, so as to generate the endoscopy report.

After that, on the basis of the log information reported from the video processor 1 through the server 5 every time an event occurs during the examination, the reporting PC 120 sets received information sequentially in a corresponding predetermined position in the endoscopy report until it receives a report indicating a termination of examination. In addition to the above-described information reported when the examination starts, the information transmitted to the reporting PC 120 as log information also includes, for example, a termination of an endoscopic examination, a start and a termination of an observation in a specific-light-observation mode such as an NBI mode, a start and a termination of an enlarged observation, and pieces of time information that indicate times at which these events occurred.

When it receives a report indicating a termination of examination and time information indicating a termination time from the video processor 1 through the server 5, the reporting PC 120 sets these pieces of information in the respective predetermined positions in the endoscopy report. In the example, items described in an endoscopy report also include an examination time, a time that was needed for an NBI observation, and a time that was needed for an enlarged observation, as illustrated in FIG. 13A. When it calculates these necessary times using a start time and a termination time of an examination, a start time and a termination time of an NBI observation, and a start time and a termination time of an enlarged observation, and sets the pieces of information in the respective positions, the reporting PC 120 terminates processing of generating an endoscopy report.

According to another aspect illustrated in FIG. 13B, during an endoscopic examination, information indicating the occurrence of each event and its time information are stored as log information in the log information storing area 32 of the nonvolatile memory 13 in the video processor 1. When the endoscopic examination has been terminated, the video processor 1 transmits the log information stored in the log information storing area 32 of the nonvolatile memory 13 to the reporting PC 120 through the server 5. The content of log information in this another aspect is similar to that in the aspect described with reference to FIG. 13A. On the basis of the log information received from the video processor 1 side after the termination of the endoscopic examination, the reporting PC 120 sets the information in each position in an endoscopy report in a predetermined format, so as to generate the endoscopy report.

In the aspect illustrated in FIG. 13B, in which log information is transmitted after an examination, for example, it is also acceptable to have a configuration in which it is possible to select, in advance, which information (event) is to be or is not to be transmitted as log information. For example, it is possible to perform a setting such as including a start of an NBI observation and its start time in the log information but not including a termination of an NBI observation and its termination time in the log information.

In the aspect of FIG. 13B, there is a possibility that the endoscopic system 100 that includes the video processor 1 will be powered off for, for example, a next examination before the video processor 1 transmits log information to the reporting PC 120. Thus, according to a variation of the aspect of FIG. 13B, the timing at which the video processor 1 transmits log information may be a timing after the video processor 1 is powered on to start. Such a usage mode of the endoscopic system 100 effectively prevents log information from remaining untransmitted.

As described above, the endoscopic system 100 according to the present embodiment permits the video processor 1 to generate log information indicating an event that occurs during an endoscopic examination, such as a start and a termination of an examination, a start and a termination of a specific light observation, and a start and a termination of an enlarged observation. The reporting PC 120 sets, in a predetermined position in a predetermined format, information included in the log information received from the video processor 1, so as to generate an endoscopy report. This permits a user such as a doctor to skip a generation of an endoscopy report after an examination, which makes it possible to improve the efficiency in an operation after the examination.

Third Embodiment

In the first or second embodiment described above, a detection of a target area of an image or a generation of an endoscopy report is respectively performed in the endoscopic system, which results in improving the efficiency in an operation after an endoscopic examination that is performed by a doctor or a nurse. On the other hand, an endoscopic system according to the present embodiment presents a recommended approach to an anomaly in vital information on a patient that occurs during an endoscopic examination, which results in improving the efficiency in an operation.

A method for presenting a recommended approach to a user when an anomaly in vital information occurs is specifically described below, the method being executed by the endoscopic system according to the present embodiment. The configuration of the endoscopic system according to the present embodiment is as described in FIG. 1 or 2 and is similar to those of the above-described embodiments, so the description is omitted.

Figure 14:
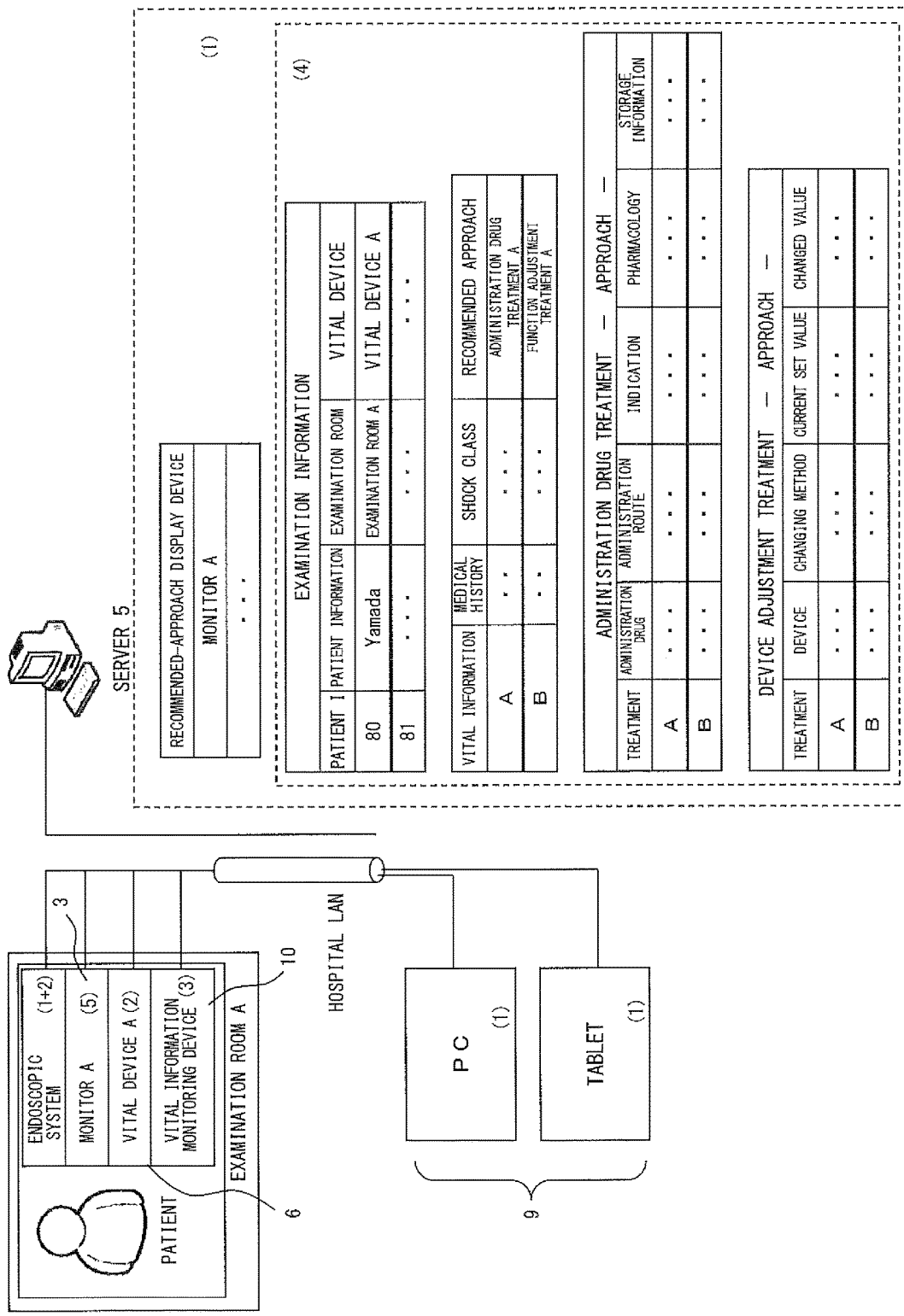
FIG. 14 is a diagram that explains a method for presenting, to a user, a recommended approach to an anomaly in vital information, the method being executed by the endoscopic system according to a third embodiment.

FIG. 14 is a diagram that explains a method for presenting, to a user, a recommended approach to an anomaly in vital information, the method being executed by the endoscopic system 100 according to the present embodiment. Compared with the configuration of the system illustrated in FIG. 1, the endoscopic system 100 according to the present embodiment is different from it in that a vital device 6 and a vital information monitoring device 10 have been added in the configuration of the endoscopic system 100 illustrated in FIG. 14. The vital device 6 is, for example, a device which is mounted on a patient (a subject), for example, during an endoscopic examination to obtain vital information on the patient by performing measurement. An input device 9 corresponds to the vital device 6 in the configuration of FIG. 14, and the vital device 6 transmits the obtained information to the vital information monitoring device 10. Blood pressure and pulse are examples of the vital information. The vital information monitoring device 10 monitors the vital information obtained from the vital device 6 so as to monitor whether they are at normal levels, and reports to the server 5 when it detects an anomaly.

In FIG. 14, each Procedure (1) to (5) is placed after a corresponding device which performs the procedure, wherein the procedures include monitoring vital information on a patient who is undergoing an endoscopic examination, determining, in the endoscopic system 100, an approach when an anomaly in the vital information has been detected, and presenting a recommended approach to a user.

First, in Procedure (1), medical history information on a patient who will undergo an endoscopic examination, shock class information, information on a recommended approach when an anomaly in vital information occurs, and information on where the recommended approach is displayed are registered in the server 5 using a PC or a tablet. The PC and the tablet correspond to the client PC 9 in FIG. 1.

The recommended approach when an anomaly in vital information occurs includes, for example, information on a drug to be administered and information on how to change, for example, a set value in a device. With respect to where a recommended approach is displayed, for example, when the endoscopic system 100 includes a plurality of monitors 3, a monitor on which a recommended approach is to be displayed is designated by a user, for example, like "monitor A". With respect to where a recommended approach is displayed, the PC or the tablet may be designated.

Further, in Procedure (1), information that identifies a patient is also registered in the server 5. The information that identifies a patient may be obtained from another system such as a patient registration system.

Furthermore, as illustrated in FIG. 14, in Procedure (1), information that identifies an examination room is associated with a vital device used for the examination, and they are registered to be examination information in the server 5.

In Procedure (2), the vital device 6 starts obtaining vital information. The vital information obtained by the vital device 6 is transmitted to the vital information monitoring device 10.

In Procedure (3), the vital information monitoring device 10 monitors the vital information, and reports to the server 5 when it detects an anomaly in, for example, a numerical value.

In Procedure (4), the server 5 performs a search in the examination information that is a database in the server 5, and derives a corresponding shock class from the vital device reported in Procedure (3) and the medical history information registered in Procedure (1). Then, the server (5) obtains a recommended approach corresponding to the derived shock class from the examination information. FIG. 14 illustrates the case in which an anomaly has been detected in a vital device A during an endoscopic examination of a patient identified by a patient ID "80", the vital device A being associated with the patient ID in the examination information of FIG. 14. In this case, with respect to the report of Procedure (3) that indicates that an anomaly has been detected in the vital information that is related to the vital device A, the server 5 obtains "vital device A" that is indicated by the vital information in the examination information, and a recommended approach that is associated with the shock class registered in Procedure (1). In FIG. 14, "administration drug treatment A" is obtained.

The server 5 refers to an administration-drug-treatment table in which the details of an administration drug treatment are registered, so as to obtain the details of the obtained "administration drug treatment A" (an administration drug, an administration route, an indication, pharmacology, and storage information).

Finally, in Procedure (5), the server 5 transmits the recommended approach obtained in Procedure (4) to a predetermined monitor 3 ("monitor A" of FIG. 14). The monitor 3 displays the information received from the server 5.

In Procedure (1) described above, information that identifies an examination room is associated with a vital device used for examination, and they are registered in the examination information in the server 5. A method for changing a set value of the vital device 6 may be used as an approach to an anomaly in the vital device 6. In this case, if the information that identifies an examination room is associated with a vital device in advance, it is possible to set an approach suitable for an examination room, that is, for an environment in which an endoscopic examination is performed.

An operation may be performed during an endoscopic examination. In this case, monitoring of whether an anomaly has occurred in vital information on a patient is performed using the vital device 6, and if an anomaly has occurred, it is necessary to deal with it. On the other hand, the method according to the present embodiment described above permits a user such as a doctor or a nurse to check a recommended approach displayed on the monitor 3 to deal with an anomaly in vital information. If a most recommended approach that is suitable for an individual patient or an environment such as an examination room is displayed on the monitor 3, the time to determine an approach to an anomaly in vital information that occurs during an endoscopic examination, or the time needed to understand a content of an approach and to execute the approach is shortened, which results in being able to improve the efficiency in an operation.

As described above, according to the embodiments above, a display on a monitor or a recording in a recording device is performed such that it is possible to recognize an area that has been determined by a doctor to be suspected of being a lesion during an endoscopic examination, which permits the improvement of the efficiency in an operation after an examination and the prevention of under diagnosis The present invention is not limited to the above-described embodiments as they are, but may be embodied by modifying constituents within a scope not deviating from the gist of the invention at a practice stage. In addition, various inventions can be made by appropriately combining a plurality of constituents that have been disclosed in the above embodiments. For example, all the constituents that have been disclosed in the embodiments may be appropriately combined. Further, constituents in different embodiments may be appropriately combined. It should be understood that various modifications and applications can be made without departing from the scope and the spirit of the invention.

What is claimed is:

1. An endoscopic processor comprising:
   a video signal input to which a video signal obtained by capturing an image of a subject is input;
   a release signal input to which a release signal created by a release manipulation performed by a user is input;
   a target area detector that is connected to the video signal input and that, for each frame image in the input video signal, detects a target area within the frame image and outputs position information, the target area being an area in which an amount of characteristics is greater than a predetermined threshold;
   a zoom processor that generates an enlarged image obtained by performing zoom processing on the target area within the frame image on the basis of the position information output by the target area detector;
   a storage that associates the enlarged image generated by the zoom processor with the frame image from which the target area has been detected and that holds the images; and
   an output that externally outputs, from the storage, the frame image and the enlarged image that both correspond to a timing at which the release signal was input to the release signal input.

2. The endoscopic processor according to claim 1, wherein the target area detector divides the frame image into a plurality of grids and detects a set of grids as the target area from the plurality of grids, wherein the amount of characteristics is greater than the predetermined threshold in each grid of the set of grids.

3. The endoscopic processor according to claim 1, wherein the target area detector calculates the amount of characteristics using a value of a level of red (R) or a color pattern when a specific light observation is performed.

4. The endoscopic processor according to claim 3, wherein when the frame image is a white-light observation image, the target area detector detects a corresponding grid as the target area from the plurality of grids if a representative value of a level of red (R) in the grid is greater than the representative value of red (R) in the frame image, and if the grid includes an edge structure.

5. The endoscopic processor according to claim 3, wherein when the frame image is a narrow-band-light observation image, the target area detector detects a corresponding grid as the target area from the plurality of grids if representative values of reflection levels of blue (B) and green (G) in the grid are respectively less than the representative values of blue (B) and green (G) in the frame image, or if representative values of absorption levels of blue (B) and green (G) in the grid are respectively greater than the representative values of absorption levels of blue (B) and green (G) in the frame image.

6. The endoscopic processor according to claim 3, wherein when the frame image is a photodynamic diagnosis image, the target area detector detects a corresponding grid as the target area from the plurality of grids if a representative value of a level of red (R) in the grid is greater than the representative value of a level of red (R) in the frame image.

7. The endoscopic processor according to claim 1, wherein the output outputs an image in which marking is performed around the target area in the frame image.

* * * * *